United States Patent
Coudert et al.

(10) Patent No.: US 7,202,255 B2
(45) Date of Patent: Apr. 10, 2007

(54) SUBSTITUTED [1,4] BENZODIOXINO[2,3-E] ISOINDOLE DERIVATIVES, METHOD FOR PREPARING AND PHARMACEUTICAL COMPOSITIONS CONTAINING SAME

(75) Inventors: Gerard Coudert, Saint Denis en Val (FR); Nathalie Ayerbe, Palavas les Flots (FR); Franck Lepifre, Olivet (FR); Sylvain Routier, Tigy (FR); Daniel-Henri Caignard, Le Pecq (FR); Pierre Renard, Le Chesnay (FR); John Hickman, Paris (FR); Alain Pierre, Les Alluets le Roi (FR); Stephane Leonce, Versailles (FR)

(73) Assignee: Les Laboratoires Servier, Courbevoie Cedex (FR)

( * ) Notice: Subject to any disclaimer, the term of this patent is extended or adjusted under 35 U.S.C. 154(b) by 6 days.

(21) Appl. No.: 10/531,393

(22) PCT Filed: Oct. 17, 2003

(86) PCT No.: PCT/FR03/03069

§ 371 (c)(1),
(2), (4) Date: Apr. 14, 2005

(87) PCT Pub. No.: WO2004/037831

PCT Pub. Date: May 6, 2004

(65) Prior Publication Data

US 2006/0040930 A1 Feb. 23, 2006

(30) Foreign Application Priority Data

Oct. 18, 2002 (FR) .................................. 02 12965

(51) Int. Cl.
*A61K 31/437* (2006.01)
*C07D 491/22* (2006.01)
(52) U.S. Cl. ..................... 514/279; 546/41; 548/417; 514/410
(58) Field of Classification Search .............. 514/279, 514/410; 546/41; 548/417
See application file for complete search history.

(56) References Cited

U.S. PATENT DOCUMENTS 5,705,511 A 1/1998 Hudkins et al.

FOREIGN PATENT DOCUMENTS

EP 0841337 5/1998
WO WO9809967 3/1998

*Primary Examiner*—Charanjit S. Aulakh
(74) *Attorney, Agent, or Firm*—Hueschen and Sage

(57) ABSTRACT

Compounds of formula (I):

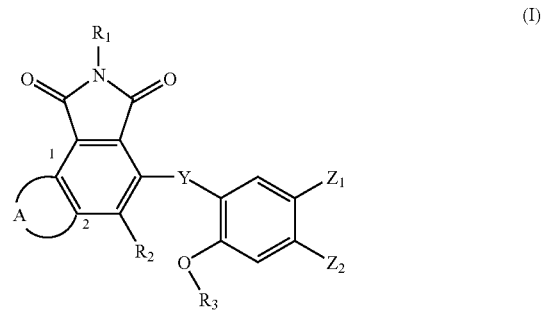

wherein:
A is as defined in the description,
Y represents a group selected from an oxygen atom and a methylene group,
$R_2$ represents a hydrogen atom and in that case:
$R_3$ represents a group selected from a hydrogen atom and the groups linear or branched ($C_1$–$C_6$)alkyl, aryl, aryl-($C_1$–$C_6$)alkyl (in which the alkyl moiety is linear or branched) and $SO_2CF_3$,
or $R_2$ and $R_3$ form a bond,
$R_1$ represents a group selected from a hydrogen atom and the groups linear or branched ($C_1$–$C_6$)alkyl, aryl and aryl-($C_1$–$C_6$)alkyl (in which the alkyl moiety is linear or branched) or a linear or branched ($C_1$–$C_6$)alkylene chain,
$Z_1$ and $Z_2$ each represent a hydrogen atom or
$Z_1$ and $Z_2$, together with the carbon atoms carrying them, form a phenyl group.
Medicaments.

12 Claims, No Drawings

SUBSTITUTED [1,4] BENZODIOXINO[2,3-E] ISOINDOLE DERIVATIVES, METHOD FOR PREPARING AND PHARMACEUTICAL COMPOSITIONS CONTAINING SAME

The present invention relates to new substituted [1,4] benzodioxino[2,3-e]isoindole compounds, to a process for their preparation and to pharmaceutical compositions containing them. Use of the compounds of the present invention is promising because of their anti-tumour activity.

Patent Application WO 00/18407 describes pyrrolocarbazole compounds for use in the prevention and treatment of deafness and the sensation of loss of balance. Patent Applications U.S. Pat. No. 5,705,511 and WO 96/11933 describe cyclopenta[g]pyrrolo[3,4-e]indole compounds fused at their indole moiety and cyclopentene moiety to an aromatic or non-aromatic cyclic system optionally containing hetero atoms. Those compounds possess pharmacological activities making them of use especially in the treatment of cancerous cells. Patent Application WO 01/85686 describes pyrrolocarbazole-aryl compounds for use in the treatment of cancers. Patent Application EP 0 841 337 claims substituted 7,12-dioxo-benzo[a]anthracene compounds and describes their anti-cancer properties.

The compounds of the present invention are novel in terms of both their structure and their use as anti-tumour agents.

More specifically, the present invention relates to compounds of formula (I):

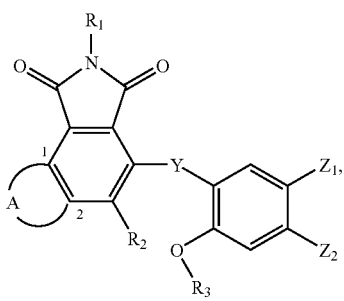

wherein:
A, together with the carbon atoms to which it is bonded, represents a group of formula (a) or (b):

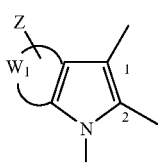

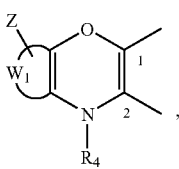

wherein:
$W_1$, together with the carbon atoms to which it is bonded, represents a phenyl group or a pyridyl group, Z represents a group selected from hydrogen and halogen atoms and the groups linear or branched $(C_1-C_6)$alkyl, nitro, cyano, hydroxy, linear or branched $(C_1-C_6)$alkoxy, aryl, aryl-$(C_1-C_6)$alkyl (in which the alkyl moiety is linear or branched), aryloxy and aryl-$(C_1-C_6)$alkoxy (in which the alkoxy moiety is linear or branched) and $NR_5R_6$ wherein $R_5$ and $R_6$, which are identical or different, each independently of the other represents a group selected from a hydrogen atom and a linear or branched $(C_1-C_6)$alkyl group, $R_4$ represents a group selected from a hydrogen atom and the groups linear or branched $(C_1-C_6)$alkyl, aryl and aryl-$(C_1-C_6)$alkyl (in which the alkyl moiety is linear or branched) or a group —C(O)—OR'$_5$ wherein R'$_5$ represents a group selected from the groups linear or branched $(C_1-C_6)$alkyl, aryl and aryl-$(C_1-C_6)$alkyl (in which the alkyl moiety is linear or branched), Y represents a group selected from an oxygen atom and a methylene group, $R_2$ represents a hydrogen atom and, in that case:
  $R_3$ represents a group selected from a hydrogen atom and the groups linear or branched $(C_1-C_6)$alkyl, aryl, aryl-$(C_1-C_6)$alkyl (in which the alkyl moiety is linear or branched) and $SO_2CF_3$, or $R_2$ and $R_3$ form a bond, $R_1$ represents a group selected from a hydrogen atom and the groups linear or branched $(C_1-C_6)$alkyl, aryl and aryl-$(C_1-C_6)$alkyl (in which the alkyl moiety is linear or branched) or a linear or branched $(C_1-C_6)$alkylene chain substituted by one or more identical or different groups selected from —OR''$_5$ and NR''$_5$R''$_6$ wherein R''$_5$ and R''$_6$ are as defined for $R_5$ and $R_6$ defined hereinbefore, $Z_1$ and $Z_2$ each represent a hydrogen atom or
  $Z_1$ and $Z_2$, together with the carbon atoms carrying them, form a phenyl group, with the proviso that, when Z represents a hydrogen atom, $R_1$ is other than a hydrogen atom, to their enantiomers, diastereoisomers, N-oxide, and to addition salts thereof with a pharmaceutically acceptable acid or base, wherein "aryl" is to be understood as meaning a phenyl, naphthyl, dihydronaphthyl, tetrahydronaphthyl, indenyl or indanyl group, each of those groups being optionally substituted by one or more identical or different groups selected from halogen, linear or branched $(C_1-C_6)$alkyl, linear or branched $(C_1-C_6)$trihaloalkyl, hydroxy, linear or branched $(C_1-C_6)$alkoxy, and amino optionally substituted by one or two linear or branched $(C_1-C_6)$alkyl groups.

Among the pharmaceutically acceptable acids there may be mentioned, without implying any limitation, hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, methanesulphonic acid, camphoric acid etc.

Among the pharmaceutically acceptable bases there may be mentioned, without implying any limitation, sodium hydroxide, potassium hydroxide, triethylamine etc.

Preferred compounds of the invention are compounds of formula (I) that correspond more especially to formula (IA):

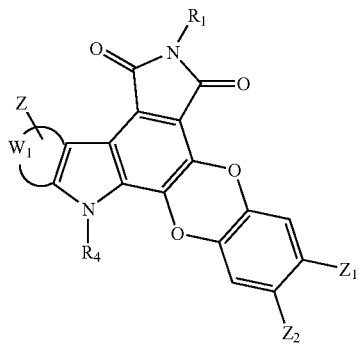
(IA)

wherein $R_1$, $R_4$, $W_1$, $Z$, $Z_1$ and $Z_2$ are as defined for formula (I).

According to a second advantageous embodiment, preferred compounds of the invention are compounds of formula (I) that correspond more especially to formula (IB):

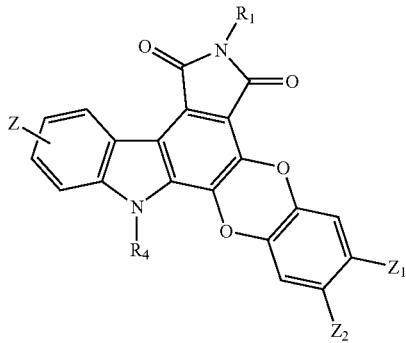
(IB)

wherein $R_1$, $R_4$, $Z$, $Z_1$ and $Z_2$ are as defined for formula (I).

According to a third advantageous embodiment, preferred compounds of the invention are compounds of formula (I) corresponding more especially to formula (IC):

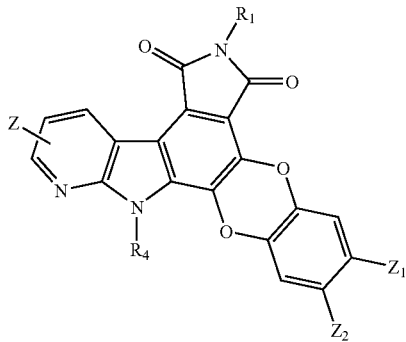
(IC)

wherein $R_1$, $R_4$, $Z$, $Z_1$ and $Z_2$ are as defined for formula (I).

According to a fourth advantageous embodiment, preferred compounds of the invention are compounds of formula (I) that correspond more especially to formula (ID):

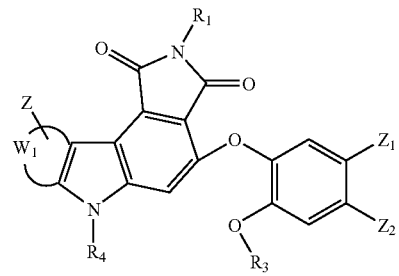
(ID)

wherein $R_1$, $R_3$, $R_4$, $W_1$, $Z$, $Z_1$ and $Z_2$ are as defined for formula (I).

According to a fifth advantageous embodiment, preferred compounds of the invention are compounds of formula (I) that correspond more especially to formula (IE):

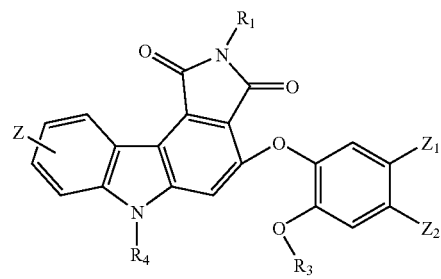
(IE)

wherein $R_1$, $R_3$, $R_4$, $Z$, $Z_1$ and $Z_2$ are as defined for formula (I).

According to a sixth advantageous embodiment, preferred compounds of the invention are compounds of formula (I) that correspond more especially to formula (IF):

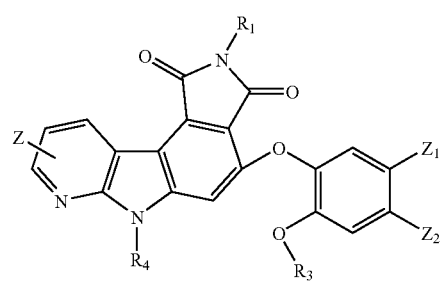
(IF)

wherein $R_1$, $R_3$, $R_4$, $Z$, $Z_1$ and $Z_2$ are as defined for formula (I).

According to a seventh advantageous embodiment, preferred compounds of the invention are compounds of formula (I) that correspond more especially to formula (IG):

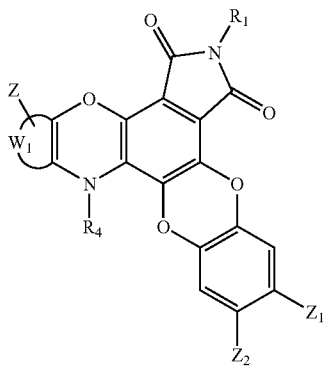

wherein $R_1$, $R_4$, $W_1$, $Z$, $Z_1$ and $Z_2$ are as defined for formula (I).

According to an eighth advantageous embodiment, preferred compounds of the invention are compounds of formula (I) that correspond more especially to formula (IH):

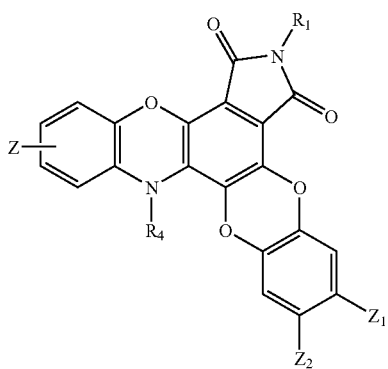

wherein $R_1$, $R_4$, $Z$, $Z_1$ and $Z_2$ are as defined for formula (I).

According to a ninth advantageous embodiment, preferred compounds of the invention are compounds of formula (I) that correspond more especially to formula (IJ):

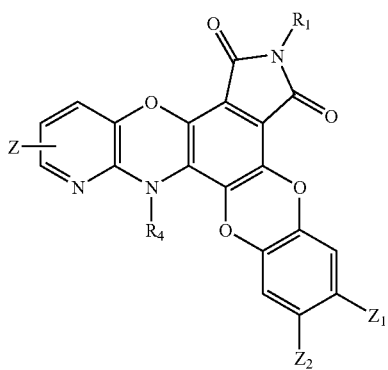

wherein $R_1$, $R_4$, $Z$, $Z_1$ and $Z_2$ are as defined for formula (I).

In one embodiment of interest, the group Z to which preference is given in accordance with the invention is a hydrogen atom, halogen atom or hydroxy group.

Advantageously, the group A, together with the carbon atoms to which it is bonded, to which preference is given in accordance with the invention, is a group of formula:

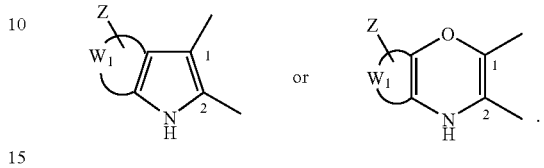

In an especially advantageous embodiment, the group $R_3$ to which preference is given in accordance with the invention is a hydrogen atom or a linear or branched $(C_1-C_6)$alkyl group.

In an especially advantageous embodiment, the group $R_1$ to which preference is given in accordance with the invention is a hydrogen atom, a linear or branched $(C_1-C_6)$alkyl group or a linear or branched $(C_1-C_6)$alkylene chain substituted by one or more identical or different groups selected from —$NR_5R_6$ wherein $R_5$ and $R_6$ are as defined for formula (I).

In another embodiment of interest, the groups $Z_1$ and $Z_2$ to which preference is given in accordance with the invention are hydrogen atoms.

Compounds to which preference is given in accordance with the invention are:

7-methyl[1,4]benzodioxino[2,3-a]pyrrolo[3,4-c]carbazole-6,8-dione, 10-fluoro-7-methyl[1,4]benzodioxino[2,3-a]pyrrolo[3,4-c]carbazole-6,8-dione, 11-fluoro-7-methyl[1,4]benzodioxino[2,3-a]pyrrolo[3,4-c]carbazole-6,8-dione, 7-[2-(dimethylamino)ethyl]-10-fluoro[1,4]benzodioxino[2,3-a]pyrrolo[3,4-c]-carbazole-6,8-dione, 10-hydroxy[1,4]benzodioxino[2,3-a]pyrrolo[3,4-c]carbazole-6,8-dione, 11-hydroxy[1,4]benzodioxino[2,3-a]pyrrolo[3,4-c]carbazole-6,8-dione, 7-[2-(dimethylamino)ethyl][1,4]benzodioxino[2,3-a]pyrrolo[3,4-c]carbazole-6,8-dione, 7-[2-(dimethylamino)ethyl]-10-hydroxy[1,4]benzodioxino[2,3-a]pyrrolo[3,4-c]-carbazole-6,8-dione, 7-[2-(dimethylamino)ethyl]-11-hydroxy[1,4]benzodioxino[2,3-a]pyrrolo[3,4-c]-carbazole-6,8-dione, 7-[2-(dimethylamino)ethyl][1,4]benzodioxino[2,3-e]pyrido[2',3':5,6][1,4]oxazino-[3,2-g]isoindole-6,8-dione.

The enantiomers, diastereoisomers, N-oxides, and addition salts with a pharmaceutically acceptable acid or base, of the preferred compounds form an integral part of the invention.

The invention relates also to a process for the preparation of compounds of formula (I), which process is characterised in that there is used as starting material a compound of formula (II):

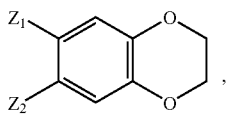
(II)

wherein $Z_1$ and $Z_2$ are as defined for formula (I), which compound of formula (II) is reacted with N-bromosuccinimide in the presence of benzoyl peroxide to yield the compound of formula (III):

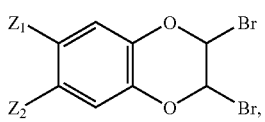
(III)

wherein $Z_1$ and $Z_2$ are as defined hereinbefore, which compound of formula (III) is reacted with sodium iodide to yield the compound of formula (IV):

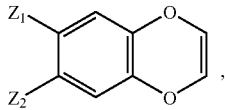
(IV)

wherein $Z_1$ and $Z_2$ are as defined hereinbefore, which compound of formula (IV) is reacted with n-butyllithium and then with trimethyltin chloride to yield the compound of formula (V):

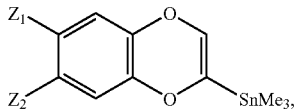
(V)

wherein $Z_1$ and $Z_2$ are as defined hereinbefore, which compound of formula (V) is:

either treated, in the presence of tetrakis(triphenylphosphine)palladium(0), with a compound of formula (VI):

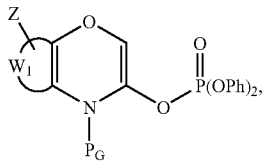
(VI)

wherein $P_G$ represents an amine-protecting group well-known in organic synthesis and $W_1$ and $Z$ are as defined for formula (I), to yield the compound of formula (VII):

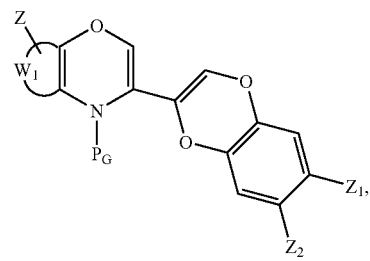
(VII)

wherein $P_G$, $Z$, $Z_1$, $Z_2$ and $W_1$ are as defined hereinbefore, which compound of formula (VII) is treated with a compound of formula (VIII):

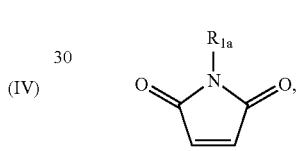
(VIII)

wherein $R_{1a}$ represents a hydrogen atom or a methyl group, to yield the compound of formula (IX):

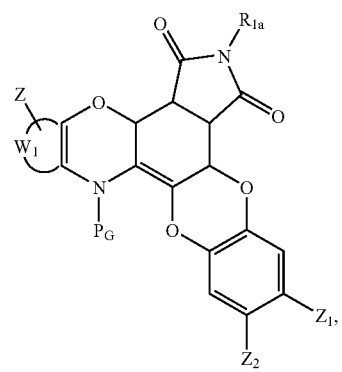
(IX)

wherein $P_G$, $R_{1a}$, $Z$, $Z_1$, $Z_2$ and $W_1$ are as defined hereinbefore, which compound of formula (IX) is treated with N-bromosuccinimide and benzoyl peroxide to yield the compound of formula (I/a), a particular case of the compounds of formula (I):

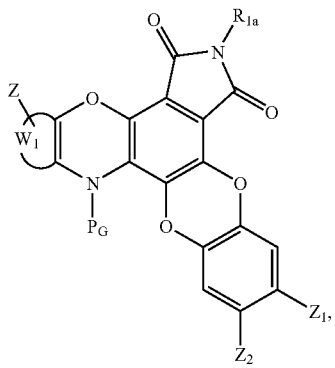

(I/a)

wherein $P_G$, $R_{1a}$, Z, $Z_1$, $Z_2$ and $W_1$ are as defined hereinbefore, which compound of formula (I/a) is optionally treated with a compound of formula (X):

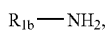

(X)

wherein $R_{1b}$ has the same definition as $R_1$ in formula (I) but is other than a hydrogen atom or a methyl group, to yield the compound of formula (I/b), a particular case of the compounds of formula (I):

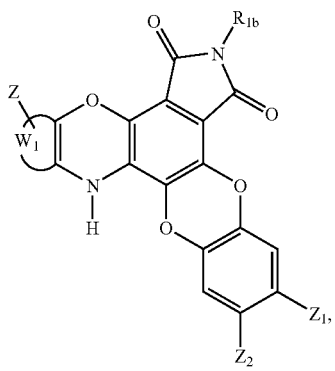

(I/b)

wherein $R_{1b}$, Z, $Z_1$, $Z_2$ and $W_1$ are as defined hereinbefore, which compounds of formulae (I/a) and (I/b) constitute the compounds of formula (I/c):

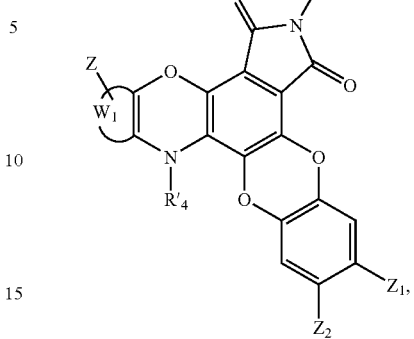

(I/c)

wherein $R'_4$ represents a hydrogen atom or a group $P_G$, and $R_1$, Z, $Z_1$, $Z_2$ and $W_1$ are as defined hereinbefore, or treated in the presence of bis(triphenylphosphine)palladium(II) chloride with a compound of formula (XI):

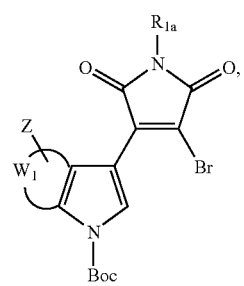

(XI)

wherein Boc represents a tert-butoxycarbonyl group and $R_{1a}$, $W_1$ and Z are as defined hereinbefore, to yield the compound of formula (XII):

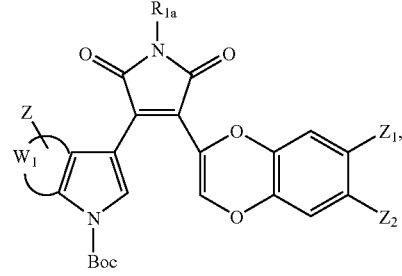

(XII)

wherein Boc, $R_{1a}$, Z, $Z_1$, $Z_2$ and $W_1$ are as defined hereinbefore, which compound of formula (XII) is:
either irradiated with a UV lamp, in the presence of iodine, in a non-polar and aprotic solvent, to yield the compounds of formulae (I/d) and (I/e), particular cases of the compounds of formula (I):

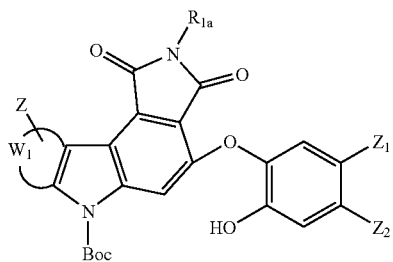

(I/d)

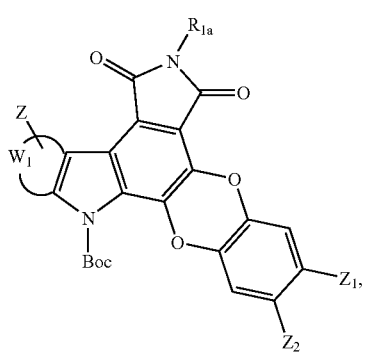

(I/e)

wherein Boc, $R_{1a}$, Z, $Z_1$, $Z_2$ and $W_1$ are as defined hereinbefore, which compounds of formula (I/d):
optionally are subjected to deprotection of the amine function according to conventional methods of organic synthesis to yield the compound of formula (I/f), a particular case of the compounds of formula (I):

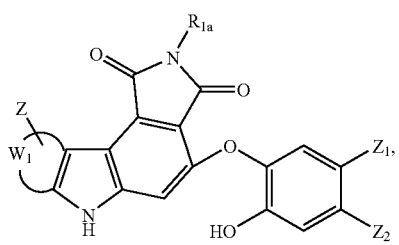

(I/f)

wherein $R_{1a}$, Z, $Z_1$, $Z_2$ and $W_1$ are as defined hereinbefore,
or optionally are subjected to the action of a compound of formula (XIII):

$R_{3a}$—G, (XIII)

wherein $R_{3a}$, has the same definition as $R_3$ in formula (I) but is other than a hydrogen atom and G is as defined hereinbefore, to yield the compound of formula (I/g), a particular case of the compounds of formula (I):

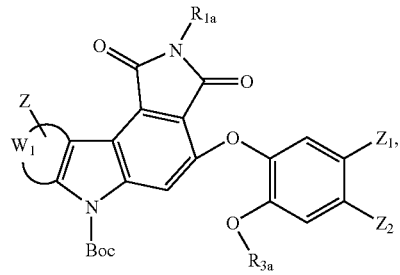

(I/g)

wherein Boc, $R_{1a}$, $R_{3a}$, Z, $Z_1$, $Z_2$ and $W_1$ are as defined hereinbefore, which compounds of formulae (I/d), (I/e) and (I/g) constitute the compound of formula (I/h):

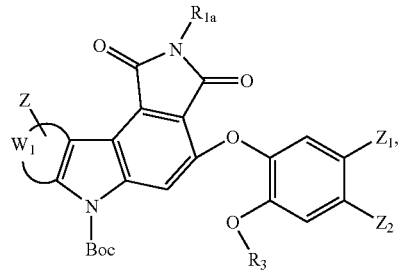

(I/h)

wherein Boc, $R_{1a}$, $R_3$, Z, $Z_1$, $Z_2$ and $W_1$ are as defined hereinbefore, which compound of formula (I/h) optionally is subjected to the same reaction conditions as the compound of formula (I/a) to yield the compound of formula (I/i), a particular case of the compounds of formula (I):

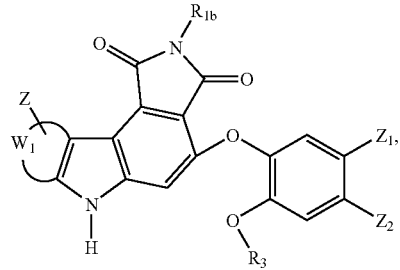

(I/i)

wherein $R_{1b}$, $R_3$, Z, $Z_1$, $Z_2$ and $W_1$ are as defined hereinbefore, or subjected to the action of hydrochloric acid to yield the compound of formula (XIV):

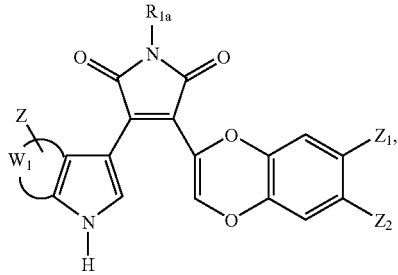
(XIV)

wherein $R_{1a}$, Z, $Z_1$, $Z_2$ and $W_1$ are as defined hereinbefore,
which compound of formula (XIV) is subjected to the action of a compound of formula (XV):

$$R_{4a}\text{—}G,\quad (XV)$$

wherein G represents a leaving group and $R_{4a}$ has the same definition as $R_4$ in formula (I) but is other than a hydrogen atom, to yield the compound of formula (XVI):

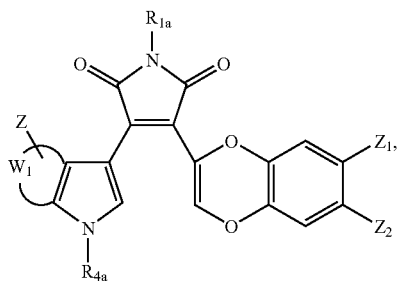
(XVI)

wherein $R_{1a}$, $R_{4a}$, Z, $Z_1$, $Z_2$ and $W_1$ are as defined hereinbefore,
which compound of formula (XVI) is subjected to the same reaction conditions as the compound of formula (XII) to yield the compounds of formulae (I/j) and (I/k), particular cases of the compounds of formula (I):

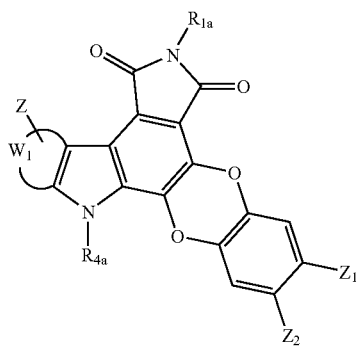
(I/j)

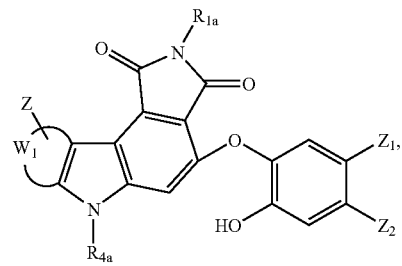
(I/k)

wherein $R_{1a}$, $R_{4a}$, Z, $Z_1$, $Z_2$ and $W_1$ are as defined hereinbefore,
which compound of formula (I/k) optionally is subjected to the action of a compound of formula (XIII) as defined hereinbefore to yield the compound of formula (I/l):

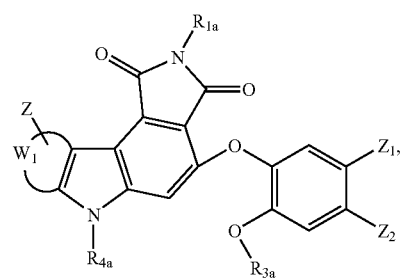
(I/l)

wherein $R_{1a}$, $R_{3a}$, $R_{4a}$, Z, $Z_1$, $Z_2$ and $W_1$ are as defined hereinbefore,
which compounds of formulae (I/j), (I/k) and (I/l) constitute the compounds of formula (I/m):

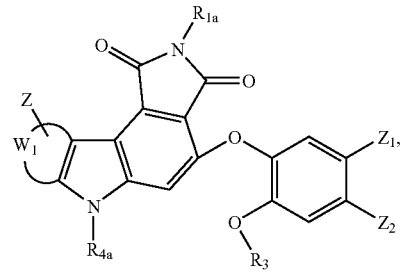
(I/m)

wherein $R_{1a}$, $R_3$, $R_{4a}$, Z, $Z_1$, $Z_2$ and $W_1$ are as defined hereinbefore,
which compound of formula (I/m) optionally is subjected to the same reaction conditions as the compound of formula (I/h) to yield the compound of formula (I/n):

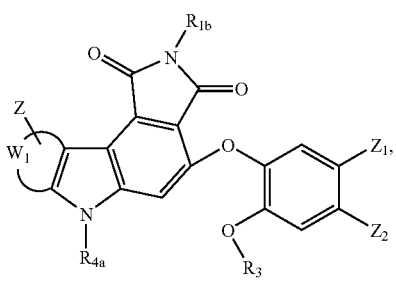

(I/n)

wherein $R_{1b}$, $R_3$, $R_{4a}$, $Z$, $Z_1$, $Z_2$ and $W_1$ are as defined hereinbefore, which compounds of formulae (I/e), (I/h) and (I/i), (I/m) and (I/n) constitute the compounds of formula (I/o):

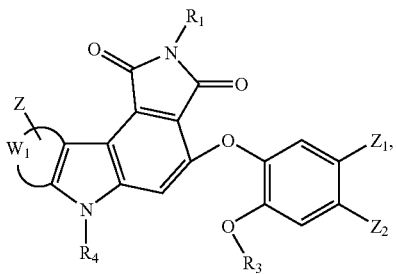

(I/o)

wherein $R_1$, $R_3$, $R_4$, $Z$, $Z_1$, $Z_2$ and $W_1$ are as defined hereinbefore, which compounds of formulae (I/a) to (I/o) constitute the totality of the compounds of formula (I), which are purified, where necessary, according to conventional purification techniques, which may be separated, if desired, into their different isomers according to a conventional separation technique, and which are converted, if desired, into their N-oxides and, where appropriate, their addition salts with a pharmaceutically acceptable acid or base.

The compounds of formula (VI) may advantageously be obtained starting from a compound of formula (A):

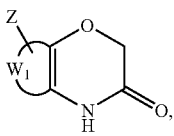

(A)

wherein Z and $W_1$ are as defined hereinbefore, the amine function of which compound of formula (A) is protected by a protecting group $P_G$ well-known to the person skilled in the art, to yield the compound of formula (B):

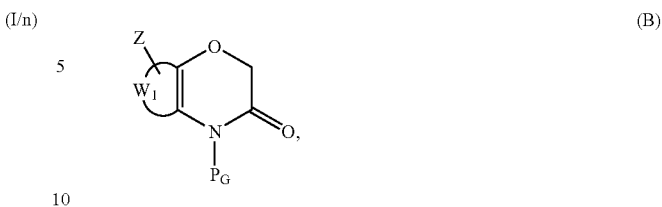

(B)

wherein $P_G$ represents a tert-butoxycarbonyl or phenoxycarbonyl group and $W_1$ and Z are as defined hereinbefore, which compound of formula (B) is treated with lithium diisopropylamide followed by diphenyl chlorophosphate to yield the compound of formula (VI).

The compounds of formula (XI) may advantageously be obtained starting from a compound of formula (C):

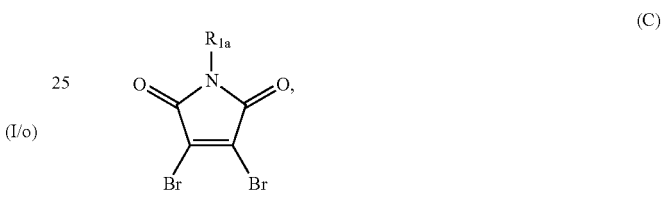

(C)

wherein $R_{1a}$ is as defined hereinbefore, which compound of formula (C) is treated, in the presence of lithium bis(trimethylsilyl)amide, with a compound of formula (D):

(D)

wherein $W_1$ and Z are as defined hereinbefore, to yield a compound of formula (E):

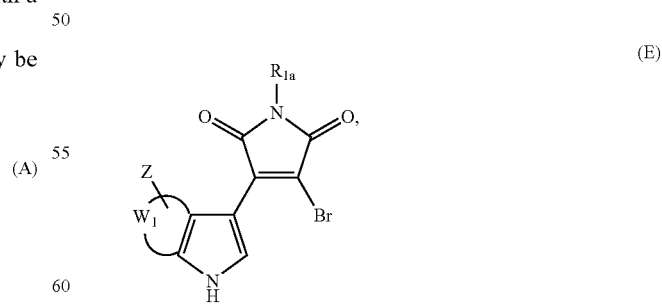

(E)

wherein $R_{1a}$, Z and $W_1$ are as defined hereinbefore, which compound of formula (E) is reacted with di-tert-butyl dicarbonate in the presence of 4-dimethylaminopyridine to yield the compound of formula (XI).

The compounds of formulae (II), (VIII), (X), (XIV), (XVI), (A), (C) and (D) either are commercial compounds or are obtained according to conventional methods of organic synthesis readily accessible to the person skilled in the art.

The compounds of formula (I) have valuable pharmacological properties. They have excellent cytotoxicity in vitro not only with respect to leukaemia lines but also with respect to solid-tumour lines; they also exert an action on the cell cycle and are active in vivo, in a leukaemia model. Those properties enable them to be used therapeutically as anti-tumour agents.

Among the types of cancer that may be treated by the compounds of the present invention there may be mentioned, without implying any limitation, adenocarcinomas and carcinomas, sarcomas, gliomas and leukaemias.

The present invention relates also to pharmaceutical compositions comprising compounds of formula (I), their enantiomers, diastereoisomers, N-oxides or an addition salt thereof with a pharmaceutically acceptable base or acid, alone or in combination with one or more inert, non-toxic excipients or carriers.

Among the pharmaceutical compositions according to the invention there may be mentioned more especially those that are suitable for oral, parenteral, nasal, rectal, perlingual, ocular or respiratory administration, and especially tablets or dragées, sublingual tablets, sachets, paquets, gelatin capsules, glossettes, lozenges, suppositories, creams, ointments, dermal gels, injectable or drinkable preparations, aerosols, eye drops and nose drops.

By virtue of the pharmacological properties that are characteristic of the compounds of formula (I), the pharmaceutical compositions comprising the said compounds of formula (I) as active ingredient are, accordingly, especially useful in the treatment of cancers.

The useful dose varies according to the age and weight of the patient, the administration route, the nature of the therapeutic indication and any associated treatments and ranges from 0.1 to 400 mg per day, in one or more administrations.

The Examples that follow illustrate the invention, without limiting it in any way. The starting materials used are known products or are prepared according to known procedures.

The structures of the compounds described in the Examples were determined according to customary spectrophotometric techniques (infra-red, nuclear magnetic resonance, mass spectrometry, . . . ).

PREPARATION A

Benzo[1,4]dioxin-2-yl(trimethyl)stannane

Step A: 2,3-Dibromo-2,3-dihydro-1,4-benzodioxine

Under an inert atmosphere, 73.45 mmol of 1,4-benzodioxane, 150 ml of carbon tetrachloride and then 163.32 mmol of recrystallised N-bromosuccinimide and 88.1 μmol of benzoyl peroxide are mixed together. The reaction mixture is refluxed with the aid of a lamp (60 W) for 6 hours. The precipitated succinimide is removed by filtration and the filtrate is concentrated, allowing the expected product to be isolated.

Step B: Benzo[1,4]dioxine 73.45 mmol of the compound obtained in Step A above are dissolved in 125 ml of acetone; the solution is then stirred for 2 hours under reflux, in the presence of sodium iodide (359.9 mmol). After evaporating off the solvent, the residue is dissolved in a mixture of water/ethyl acetate (100 ml/200 ml). The organic phase is then washed with 20% aqueous sodium thiosulphate solution and then the aqueous phase is extracted twice with ethyl acetate. The organic phases are combined, dried over magnesium sulphate and then concentrated to dryness. Purification by chromatography over silica gel (petroleum ether/ethyl acetate: 95/5) allows the expected product to be obtained.

IR (NaCl film): $v_{(C=C\ enol\ ether)}=1665$ cm$^{-1}$; $v_{(C=C\ Ar)}=1590$ cm$^{-1}$.

Step C: Benzo[1,4]dioxin-2-yl(trimethyl)stannane 14.91 mmol of 1,4-benzodioxine are dissolved in 18 ml of anhydrous tetrahydrofuran under an anhydrous atmosphere, and the temperature of the solution is lowered to −78° C. 23.86 mmol of a 1.5M solution of n-butyllithium in hexane are added dropwise to the reaction mixture, which is stirred at −78° C. for 2 hours 15 minutes. 37.28 mmol of trimethyltin chloride dissolved in 10 ml of anhydrous tetrahydrofuran are added dropwise and the reaction mixture is stirred at −78° C. for 45 minutes and then returned to ambient temperature for 15 hours. The reaction mixture is hydrolysed with 15% aqueous potassium fluoride solution and is stirred for 45 minutes. The precipitated tin salts are removed by filtration, and the aqueous phase is extracted 3 times with ethyl acetate. The organic phases are combined and concentrated. Purification by flash chromatography over silica gel (petroleum ether/ethyl acetate: 95/5) allows the expected product to be obtained.

IR (NaCl film): $v_{(C=C\ enol\ ether)}=1639$ cm$^{-1}$; $v_{(C=C\ Ar)}=1592$ cm$^{-1}$.

PREPARATION B

Naphtho[2,3-b][1,4]dioxin-2-yl(tributyl)stannane

Step A: Ethyl 2,3-dihydronaphtho[2,3-b][1,4]dioxine-2-carboxylate

Under an inert atmosphere, 47.03 mmol of dry potassium carbonate are added to a solution of 62.43 mmol of 2,3-dihydroxynaphthalene in 150 ml of anhydrous acetone. The reaction mixture is heated at reflux, after adding 17.2 mmol of ethyl 2,3-dibromopropanoate. 15 minutes later, 47.03 mmol of dry potassium carbonate, and also 17.2 mmol of ethyl 2,3-dibromopropanoate are again added to the reaction mixture. This operation is repeated two more times, at 15-minute intervals. Refluxing is maintained for 18 hours. The reaction mixture is then filtered, and the residue is washed with acetone. The filtrate is concentrated and is then taken up in ethyl acetate and washed with 100 ml of water. The aqueous phase is extracted three times with ethyl acetate, and then the organic phases are combined, dried over magnesium sulphate, filtered and evaporated under reduced pressure. Purification by flash chromatography over silica gel (petroleum ether/ethyl acetate: 9/1) allows the expected product to be isolated.

IR(NaCl film): $v_{C=O}=1759$ cm$^{-1}$. Mass spectrum: 259 [M+1]$^+$.

Step B: Ethyl naphtho[2,3-b][1,4]dioxin-2-carboxylate

Under an inert atmosphere, a solution of 25.94 mmol of the compound obtained in Step A above in 120 ml of carbon tetrachloride is heated at reflux with the aid of a lamp (60 W) in the presence of 57.03 mmol of recrystallised N-bromosuccinimide and a catalytic amount of benzoyl peroxide. Stirring is maintained at reflux for 2 hours 30 minutes. After cooling, the liberated succinimide is filtered off and the filtrate is concentrated to dryness in vacuo. The dibrominated ester obtained is dissolved in 100 ml of acetone, and then 129.62 mmol of sodium iodide are added. Stirring is maintained at ambient temperature for 4 hours. After evaporating off the solvent, the residue is taken up in a mixture of water/ethyl acetate and washed with 1M aqueous sodium thiosulphate solution. The organic phase is dried over magnesium sulphate, filtered and evaporated. Purification by flash chromatography over silica gel (petroleum ether/ethyl acetate: 9/1) allows the expected product to be isolated.

Melting point: 98° C. IR (KBr): $v_{C=O}$=1724 cm$^{-1}$; $v_{C=C}$=1682 cm$^{-1}$. Mass spectrum: 257 [M+1]$^+$.

Step C: Naphtho[2,3-b][1,4]dioxin-2-carboxylic acid

A solution of 24.58 mmol of the compound obtained in Step B above, in 25 ml of methanol, is heated at reflux for one hour, in the presence of 20 ml of 1M aqueous lithium hydroxide solution. After cooling, and evaporating off the methanol, the reaction mixture is acidified with 1M aqueous hydrochloric acid solution until a pH=1 is obtained. The precipitate formed is filtered off, allowing the expected product to be isolated.

Melting point: >360° C. IR (KBr): $v_{C=O}$=1678 cm$^{-1}$; $v_{C=C}$=1661 cm$^{-1}$; $v_{OH}$=3450 cm$^{-1}$. Mass spectrum: 229 [M+1]$^+$.

Step D: Naphtho[2,3-b][1,4]dioxine

A solution of 0.66 mmol of the compound obtained in Step C above, in 1 ml of quinoline, is heated at 220° C. for 3 hours, in the presence of a catalytic amount of powdered copper. After cooling, the residue is taken up in ethyl acetate and washed with 1M aqueous hydrochloric acid solution. The organic phase is dried over magnesium sulphate, filtered and concentrated. Purification by flash chromatography over silica gel (petroleum ether/ethyl acetate: 9/1) allows the expected product to be obtained.

Melting point: 96–98° C. IR (KBr): $v_{C=C}$=1665 cm$^{-1}$; $v_{C=O}$1296 cm$^{-1}$.

Step E:
Naphtho[2,3-b][1,4]dioxin-2-yl(tributyl)stannane

The expected product is obtained according to the procedure described in Step C of Preparation A, starting from the compound of Step D above and tributyltin chloride. IR (NaCl film): $v_{C=O}$=1166, 1247 cm$^{-1}$. Mass spectrum: 473 [M+1]$^+$.

PREPARATION C

Phenyl 3-[(diphenoxyphosphoryl)oxy]-4H-1,4-benzoxazine-4-carboxylate

Step A: Phenyl 2,3-dihydro-4H-1,4-benzoxazin-3-one-4-carboxylate

Under an anhydrous atmosphere, a solution of 10 mmol of 2H-1,4-benzoxazin-3-one in 50 ml of tetrahydrofuran is cooled to −78° C. At that temperature, 11 mmol of a 1.6M solution of n-butyllithium in hexane are added dropwise. After being in contact for 30 minutes at −78° C., 11 mmol of phenyl chloroformate are added dropwise and stirring is carried out for a further 2 hours. After returning to ambient temperature, the solution is hydrolysed and then extracted with ethyl acetate. The organic phase is dried over magnesium sulphate, filtered and evaporated. After purification by chromatography over silica gel (petroleum ether/ethyl acetate: 8/2), the expected product is isolated.

IR (NaCl film): $v_{C=O}$=1739, 1796 cm$^{-1}$. Mass spectrum: 270 (M+1).

Step B: Phenyl 3-[(diphenoxyphosphoryl)oxy]-4H-1,4-benzoxazine-4-carboxylate

Under an anhydrous atmosphere, a solution of 10 mmol of the product obtained in Step A above, in 50 ml of anhydrous THF, is cooled to −78° C. At that temperature, 12 mmol of 2M LDA (in a solution of heptane/THF) are added dropwise. After stirring for 2 hours, 12 mmol of diphenyl chlorophosphate are added dropwise to the reaction mixture, which is kept for a further 2 hours at −78° C. After returning to ambient temperature, the solution is hydrolysed and then extracted with ethyl acetate. The organic phase is dried over magnesium sulphate, filtered and concentrated. After purification of the residue by chromatography over silica gel (petroleum ether/ethyl acetate: 9/1), the expected product is isolated.

IR (NaCl film): $v_{C=O}$=1748 cm$^{-1}$; $v_{P=O}$=1315 cm$^{-1}$. Mass spectrum: 502 (M+1).

PREPARATION D

Phenyl 3-[(diphenoxyphosphoryl)oxy]-2,3-dihydro-4H-pyrido-[3,2-b][1,4]oxazine-4-carboxylate Step A: Phenyl 2,3-dihydro-4H-pyrido[3,2-b][1,4]oxazine-4-carboxylate The expected product is obtained according to the procedure described in Step A of Preparation C, using phenyl chloroformate as substrate.

Melting point: 97° C. IR (KBr): $v_{C=O}$=1717 cm$^{-1}$; 1803 cm$^{-1}$. Mass spectrum: m/z 271 (M+1).

Step B: Phenyl 3-[(diphenoxyphosphoryl)oxy]-2,3-dihydro-4H-pyrido[3,2-b][1,4]-oxazine-4-carboxylate The expected product is obtained according to the procedure described in Step B of Preparation C, starting from the compound of the Step above.

Melting point: 82° C. IR (KBr): $v_{C=O}$=1749 cm$^{-1}$; $v_{P=O}$ 1294 cm$^{-1}$. Mass spectrum: m/z 503 (M+1).

PREPARATION E

3-Bromo-4-(1H-1-carboxylate of tert-butyl-indol-3-yl)-1-methyl-1H-pyrrole-2,5-dione Step A: 3-Bromo-4-(1H-indol-3-yl)-1-methyl-1H-pyrrole-2,5-dione 11.16 mmol of indole are dissolved in 29 ml of anhydrous tetrahydrofuran under an inert atmosphere. The temperature of the reaction mixture is lowered to −15° C., and then 17.85 mmol of a 1M solution of bis(trimethylsilyl)lithium in hexane are added dropwise. After stirring at −15° C. for 1 hour 10 minutes, 7.44 mmol of 2,3-dibromo-N-methyl-maleimide dissolved in 8 ml of anhydrous tetrahydrofuran are added to the reaction mixture, which is then stirred for 20 minutes at −15° C., and for 15 minutes from −15° C. to ambient temperature. The reaction mixture is hydrolysed with a few millilitres of aqueous 0.3N hydrochloric acid solution until a pH of about 7 is obtained. A few millilitres of ethyl acetate are then added, and the aqueous phase is extracted four times with ethyl acetate. The organic phases are combined, washed with saturated aqueous sodium chloride solution and then evaporated. The residue is washed, filtered and rinsed with methanol, allowing the expected product to be isolated.

Melting point: 167° C. (decomposition). IR (KBr): $\nu_{C=O}$=1715, 1767 cm$^{-1}$; $\nu_{NH}$=3304 cm$^{-1}$. Mass spectrum: 305 [M+1]$^+$.

Step B: 3-Bromo-4-(1H-1-carboxylate of tert-butyl-indol-3-yl)-1-methyl-1H-pyrrole-2,5-dione 8.19 mmol of the compound obtained in Step A above are dissolved, at 0° C., in 37.5 ml of anhydrous tetrahydrofuran, in the presence of 28.68 mmol of di-tert-butyl dicarbonate and 614.5 μmol of 4-dimethylaminopyridine. The reaction mixture is brought to ambient temperature and stirred for 2 hours 30 minutes. After evaporating off the solvent, the residue obtained is taken up in methanol, filtered, rinsed with methanol and then dried in vacuo, allowing the expected product to be isolated.

Melting point: 142° C. IR (KBr): $\nu_{C=O}$=1762 cm$^{-1}$. Mass spectrum: 405 [M+1]$^+$.

PREPARATION F

3-Bromo-4-(1H-indol-3-yl)-1H-pyrrole-2,5-dione 15.69 mmol of indole are dissolved in 25 ml of anhydrous tetrahydrofuran under an inert atmosphere. 15.69 mmol of a 3M solution of ethylmagnesium bromide in diethyl ether are added, and the reaction mixture is heated at 60° C. for 1 hour 30 minutes. Once it has cooled, the mixture is added dropwise to a solution of 3.92 mmol of 2,3-dibromomaleimide in 6 ml of anhydrous tetrahydrofuran, and then the reaction mixture is stirred at ambient temperature for one hour. The reaction mixture is hydrolysed using 20 ml of 0.3N aqueous hydrochloric acid solution until a pH of 8.5 is obtained, and a few millilitres of ethyl acetate are added. The aqueous phase is extracted three times with ethyl acetate; the organic phases are then combined, washed with saturated aqueous sodium chloride solution and then evaporated to dryness in vacuo. The residue is washed, filtered and rinsed with methanol, allowing the expected product to be isolated.

Melting point: >300° C. IR (KBr): $\nu_{C=O}$=1772 cm$^{-1}$; $\nu_{NH}$=3343, 3699 cm$^{-1}$. Mass spectrum: 291 [M+1]$^+$.

PREPARATION G

3-Bromo-4-(5-fluoro-1H-indol-3-yl)-1-methyl-1H-pyrrole-2,5-dione

The expected product is obtained according to the procedure described in Step A of Preparation E, using 5-fluoroindole.

Melting point: >300° C. IR (KBr): $\nu_{C=O}$=1705 cm$^{-1}$; $\nu_{NH}$=3358 cm$^{-1}$. Mass spectrum: 323 [M+1]$^+$.

PREPARATION H

3-Bromo-4-(6-fluoro-1H-indol-3-yl)-1-methyl-1H-pyrrole-2,5-dione

The expected product is obtained according to the procedure described in Step A of Preparation E, using 6-fluoroindole.

Melting point: 201° C. IR (KBr: $\nu_{C=O}$=1701, 1767 cm$^{-1}$; $\nu_{NH}$=3312 cm$^{-1}$. Mass spectrum: 323 [M+1]$^+$.

PREPARATION I

3-Bromo-4-(5-fluoro-1H-indol-3-yl)-1H-pyrrole-2,5-dione

The expected product is obtained according to the procedure described in Preparation F, using 5-fluoroindole.

Melting point: 219° C. (decomposition). IR (KBr): $\nu_{C=O}$=1723, 1769 cm$^{-1}$; $\nu_{NH}$=3358 cm$^{-1}$. Mass spectrum: 309.5 [M+1]$^+$.

PREPARATION J

3-Bromo-4-(6-fluoro-1H-indol-3-yl)-1H-pyrrole-2,5-dione

The expected product is obtained according to the procedure described in Preparation F, using 6-fluoroindole.

Melting point: 199° C. (decomposition). IR (KBr): $\nu_{C=O}$=1723, 1778 cm$^{-1}$; $\nu_{NH}$=3329 cm$^{-1}$. Mass spectrum: 309 [M+1]$^+$.

PREPARATION K tert-Butyl 5-(benzyloxy)-3-(4-bromo-1-methyl-2,5-dioxo-2,5-dihydro-1H-pyrrol-3-yl)-1H-indole-1-carboxylate Step A: 3-[5-(Benzyloxy)-1H-indol-3-yl]-4-bromo-1-methyl-1H-pyrrole-2,5-dione The expected product is obtained according to the procedure described in Step A of Preparation E, using 5-benzyloxyindole.

Melting point: 150° C. (decomposition). IR (KBr): $\nu_{C=O}$=1698 cm$^{-1}$; $\nu_{NH}$=3315 cm$^{-1}$. Mass spectrum: 411 [M+1]$^+$.

Step B: tert-Butyl 5-(benzyloxy)-3-(4-bromo-1-methyl-2,5-dioxo-2,5-dihydro-1H-pyrrol-3-yl)-1H-indole-1-carboxylate The expected product is obtained according to the procedure described in Step B of Preparation E, starting from the compound of Step A above.

Melting point: 155° C. IR (KBr): $\nu_{C=O}$=1709, 1738, 1773 cm$^{-1}$. Mass spectrum: 511 [M+1]$^+$.

PREPARATION L tert-Butyl 6-(benzyloxy)-3-(4-bromo-1-methyl-2,5-dioxo-2,5-dihydro-1H-pyrrol-3-yl)-1H-indole-1-carboxylate

Step A: 3-[6-(Benzyloxy)-1H-indol-3-yl]-4-bromo-1-methyl-1H-pyrrole-2,5-dione The expected product is obtained according to the procedure described in Step A of Preparation E, using 6-benzyloxyindole.

Melting point: 138° C. (decomposition). IR (KBr): $\nu_{C=O}$=1705, 1762 cm$^{-1}$; $\nu_{NH}$=3314 cm$^{-1}$. Mass spectrum: 411 [M+1]$^+$.

Step B: tert-Butyl 6-(benzyloxy)-3-(4-bromo-1-methyl-2,5-dioxo-2,5-dihydro-1H-pyrrol-3-yl)-1H-indole-1-carboxylate The expected product is obtained according to the procedure described in Step B of Preparation E, starting from the compound of Step A above.

Melting point: 158° C. (decomposition). IR (KBr): $\nu_{C=O}$=1715, 1737, 1745 cm$^{-1}$. Mass spectrum: 511 [M+1]$^+$.

PREPARATION M tert-Butyl 5-(benzyloxy)-3-[4-bromo-1-(tert-butoxycarbonyl)-2,5-dioxo-2,5-dihydro-1H-pyrrol-3-yl]-1H-indole-1-carboxylate

Step A: 3-[5-(Benzyloxy)-1H-indol-3-yl]-4-bromo-1H-pyrrole-2,5-dione

The expected product is obtained according to the procedure described in Preparation F, using 5-benzyloxyindole.

Melting point: 154° C. (decomposition). IR (KBr): $\nu_{C=O}$=1697 cm$^{-1}$; $\nu_{NH}$=3333 cm$^{-1}$. Mass spectrum: 397 [M+1]$^+$.

Step B: tert-Butyl 5-(benzyloxy)-3-[4-bromo-1-(tert-butoxycarbonyl)-2,5-dioxo-2,5-dihydro-1H-pyrrol-3-yl]-1H-indole-1-carboxylate The expected product is obtained according to the procedure described in Step B of Preparation E, starting from the compound of Step A above.

Melting point: 134° C. IR (KBr): $\nu_{C=O}$=1743, 1768, 1801 cm$^{-1}$. Mass spectrum: 495 [M-Boc]$^+$.

PREPARATION N tert-Butyl 6-(benzyloxy)-3-[4-bromo-1-(tert-butoxycarbonyl)-2,5-dioxo-2,5-dihydro-1H-pyrrol-3-yl]-1H-indole-1-carboxylate

Step A: 3-[6-(Benzyloxy)-1H-indol-3-yl]-4-bromo-1H-pyrrole-2,5-dione

The expected product is obtained according to the procedure described in Preparation F, using 6-benzyloxyindole.

Melting point: 166° C. (decomposition). IR (KBr): $\nu_{C=O}$=1697, 1762 cm$^{-1}$; $\nu_{NH}$=3353 cm$^{-1}$. Mass spectrum: 397 [M+1]$^+$.

Step B: tert-Butyl 6-(benzyloxy)-3-[4-bromo-1-(tert-butoxycarbonyl)-2,5-dioxo-2,5-dihydro-1H-pyrrol-3-yl]-1H-indole-1-carboxylate The expected product is obtained according to the procedure described in Step B of Preparation E, starting from the compound of Step A above.

Melting point: 120° C. IR (KBr): $\nu_{C=O}$=1719, 1744, 1764, 1807 cm$^{-1}$.

PREPARATION O tert-Butyl 7-(benzhydryloxy)-3-(4-bromo-1-methyl-2,5-dioxo-2,5-dihydro-1H-pyrrol-3-yl)-1H-indole-1-carboxylate

Step A: 1-(Benzhydryloxy)-2-nitrobenzene

To a solution of dry ortho-nitrophenol (79 mmol) in 200 ml of acetone there are added 127 mmol of potassium carbonate and also 79 mmol of diphenylmethane bromide. The reaction mixture is heated at reflux for 6 hours and, after the temperature has been lowered to ambient temperature, is stirred further overnight. The reaction mixture is filtered and rinsed with acetone. The filtrate is evaporated and then taken up in diethyl ether and hydrolysed. The aqueous phase is extracted with diethyl ether; the organic phase is then dried over magnesium sulphate, filtered and concentrated. The residue obtained is taken up in petroleum ether, filtered, rinsed with petroleum ether and then dried in vacuo, allowing the expected product to be isolated.

Melting point: 98° C. Mass spectrum: 323 [M+NH$_4^+$]$^+$.

Step B: 7-(Benzhydryloxy)-1H-indole 11.95 mmol of the compound obtained in Step A above are dissolved, under an inert atmosphere, in 80 ml of anhydrous tetrahydrofuran. The temperature of the reaction mixture is then lowered to −40° C. and then 41.84 mmol of a 1M solution of vinylmagnesium bromide in tetrahydrofuran are added dropwise to the solution, which is then stirred for 2 hours 50 minutes from −40° C. to 0° C. The reaction mixture is then hydrolysed at 0° C. using 100 ml of a saturated aqueous ammonium chloride solution, and the aqueous phase is extracted three times with ethyl acetate. The organic phases are combined, dried over magnesium sulphate, filtered and evaporated. Purification by flash chromatography over silica gel (petroleum ether/ethyl acetate: 9/1) allows the expected product to be isolated.

Melting point: 114° C. (decomposition). IR Kr): $\nu_{NH}$=3425 cm$^{-1}$. Mass spectrum 300 [M+1]$^+$.

Step C: 3-[7-(Benzhydryloxy)-1H-indol-3-yl]-4-bromo-1-methyl-1H-pyrrole-2,5-dione The expected product is obtained according to the procedure described in Step A of Preparation E, using the compound of Step B above.

Melting point: 205° C. IR (KBr): $\nu_{C=O}$=1699, 1763 cm$^{-1}$; $\nu_{NH}$=3345 cm$^{-1}$. Mass spectrum: 487 [M+1]$^+$.

Step D: tert-Butyl 7-(benzhydryloxy)-3-(4-bromo-1-methyl-2,5-dioxo-2,5-dihydro-1H-pyrrol-3-yl)-1H-indole-1-carboxylate The expected product is obtained according to the procedure described in Step B of Preparation E, starting from the compound of Step C above.

Melting point: 148° C. (decomposition). IR (KBr): $\nu_{C=O}$=1709, 1759 cm$^{-1}$. Mass spectrum: 587 [M+1]$^+$.

EXAMPLE 1

Phenyl 7-methyl-6,8-dioxo-7,8-dihydro[1,4]benzo-dioxino[2,3-a]-pyrrolo[3,4-c]phenoxazine-15(6H) carboxylate

Step A: Phenyl 3-(1,4-benzodioxin-2-yl)-4H-1,4-benzoxazine-4-carboxylate

Under an inert atmosphere, a mixture of 1 mmol of the compound of Preparation C, 2 mmol of the compound of Preparation A, 3 mmol of lithium chloride and tetrakis (triphenylphosphine)palladium(0) 5% in 5 ml of tetrahydrofuran is heated at reflux. After cooling and concentrating, the residue is taken up in ethyl acetate and washed with saturated sodium chloride solution. The organic phase is dried over magnesium sulphate, filtered and concentrated. Purification by chromatography over silica gel (petroleum ether/ethyl acetate: 6/4) allows the expected product to be isolated.

Melting point: 75° C. (gum). IR (KBr): $v_{C=O}$=1739 cm$^{-1}$. Mass spectrum: 386 [M+1]$^+$.

Step B: Phenyl 7-methyl-6,8-dioxo-5b,6,7,8,8a,8b-hexahydro[1,4]benzo-dioxino[2,3-a]pyrrolo[3,4-c]phenoxazine-15(5aH)-carboxylate In a closed system, 1 mmol of the compound obtained in Step A above and 3 mmol of N-methylmaleimide are stirred at 95° C. for 2 hours in the presence of a few drops of toluene. Purification by chromatography over silica gel (petroleum ether/ethyl acetate: 3/7) allows the expected product to be obtained.

Melting point: >250° C. IR (KBr): $v_{C=O}$=1709, 1769 cm$^{-1}$. Mass spectrum: 497 [M+1]$^+$.

Step C: Phenyl 7-methyl-6,8-dioxo-7,8-dihydro[1,4 benzodioxino[2,3-a]-pyrrolo[3,4-c]phenoxazine-15(6H)-carboxylate Under an inert atmosphere, 1 mmol of the compound obtained in Step B above and 3 mmol of recrystallised N-bromosuccinimide are heated in distilled carbon tetrachloride at reflux for 7 minutes with the aid of a lamp (60 W), in the presence of a catalytic amount of benzoyl peroxide. After cooling, the solution is filtered and concentrated. Purification by chromatography over silica gel (petroleum ether/ethyl acetate: 1/1) allows the expected product to be obtained.

Melting point: 130° C. (gum). IR (KBr): $v_{C=O}$=1714, 1745 cm$^{-1}$. Mass spectrum: 493 [M+1]$^+$.

EXAMPLE 2

7-[2-(Dimethylamino)ethyl][1,4]benzodioxino[2,3-a] pyrrolo[3,4-c]-phenoxazine-6,8(7H,15H)-dione Under an inert atmosphere, 0.1 mmol of the compound of Example 1 in 2 ml of N,N-dimethylethylenediamine is heated at 100° C. for 6 hours. After cooling, the solution is concentrated. Purification by chromatography over silica gel (dichloromethane/methanol 8/2) allows the expected product to be obtained.

Melting point: 150° C. IR (KBr): $v_{C=O}$=1701, 1751 cm$^{-1}$; $v_{NH}$=3423 cm$^{-1}$. Mass spectrum: 430 [M+1]$^+$.

EXAMPLE 3

Phenyl 7-methyl-6,8-dioxo-7,8-dihydro[1,4]benzo-dioxino[2,3-e]-pyrido[2',3':5,6][1,4]oxazino[3,2-g] isoindole-15(6H)-carboxylate

Step A: Phenyl 3-(1,4-benzodioxin-2-yl)$_4$H-pyrido [3,2-b][1,4]oxazine-4-carboxylate The expected product is obtained according to the procedure described in Step A of Example 1, starting from the compound of Preparation D.

Melting point: 142° C. IR (KBr): $v_{C=O}$=1741 cm$^{-1}$. Mass spectrum: 387 [M+1]$^+$.

Step B: Phenyl 7-methyl-6,8-dioxo-5b,6,7,8,8a,8b-hexahydro[1,4]benzodioxino-[2,3-e]pyrido[2',3':5,6] [1,4]oxazino[3,2-g]isoindole-15(5aH)-carboxylate The expected product is obtained according to the procedure described in Step B of Example 1, starting from the compound of Step A above.

Melting point: 245° C. IR (KBr): $v_{C=O}$=1709, 1769 cm$^{-1}$. Mass spectrum: 498 [M+1]$^+$.

Step C: Phenyl 7-methyl-6,8-dioxo-7,8-dihydro[1,4] benzodioxino[2,3-e]pyrido-(2',3':5,6][1,4]oxazino[3, 2-g]isoindole-15(6H)-carboxylate The expected product is obtained according to the procedure described in Step C of Example 1, starting from the compound obtained in Step B above.

Melting point: >250° C. IR (KBr): $v_{C=O}$=1711, 1760 cm$^{-1}$. Mass spectrum: 494 [M+1]$^+$.

EXAMPLE 4

7-[2-(Dimethylamino)ethyl][1,4]benzodioxino[2,3-e] pyrido[2',3':5,6]-[1,4]oxazino[3,2-g]isoindole-6,8 (7H,15H)-dione The expected product is obtained according to the procedure of Example 2, starting from the compound of Example 3.

Melting point: 150° C. (decomposition). IR (KBr): $v_{C=O}$=1703, 1759 cm$^{-1}$; $v_{NH}$=3433 cm$^{-1}$. Mass spectrum: 431 [M+1]$^+$.

EXAMPLE 5 tert-Butyl 7-methyl-6,8-dioxo-7,8-dihydro[1,4]benzodioxino[2,3-a]-pyrrolo[3,4-c]carbazole-13(6H)-carboxylate

Step A: tert-Butyl 3-[4-(1,4-benzodioxin-2-yl)-1-methyl-2,5-dioxo-2,5-dihydro-1H-pyrrol-3-yl]-1H-indole-1-carboxylate To a solution of 592.23 µmol of the compound of Preparation A in 10 ml of 1,4-dioxane there are added 493.52 µmol of the compound of Preparation E, 49.35 µmol of copper iodide and 49.35 µmol of tetrakis(triphenylphosphine)palladium. The reaction mixture is heated at 100° C. for 3 hours 35 minutes, under an inert atmosphere. The solution is then filtered in order to remove the remnants of palladium, and the filtrate is evaporated. Purification by flash chromatography over silica gel (petroleum ether/ethyl acetate/triethylamine: 8/1.9/0.1) allows the expected product to be obtained.

Melting point: 140° C. IR (KBr): $v_{C=O}$=1704, 1740 cm$^{-1}$. Mass spectrum: 459 [M+1]$^+$.

Step B: tert-Butyl 7-methyl-6,8-dioxo-7,8-dihydro [1,4]benzodioxino[2,3-a]-pyrrolo[3,4-c]carbazole-13 (6H)-carboxylate 218.1 μmol of the compound obtained in Step A above and 5.91 mmol of double-sublimed iodine are dissolved in 500 ml of toluene inside the cell of an irradiation apparatus. After irradiating for 30 minutes, with stirring, the reaction mixture is cooled and then diluted with ethyl acetate. Washing with 80 ml of 20% aqueous sodium thiosulphate solution is carried out until the organic phase is decolourised. The aqueous phase is extracted with ethyl acetate three times, and then the organic phases are combined and directly concentrated in vacuo. A brown, semi-oily, semi-solid residue is collected. The procedure is repeated a further five times in the same manner, using the same amounts. The crude reaction products of the six procedures are combined. Washing with ethyl acetate is carried out on the six crude reaction products, which are then filtered. The filtrate is evaporated and then taken up in methanol, filtered, rinsed with methanol and then dried in vacuo, allowing the expected product to be isolated.

Melting point: 189° C. (decomposition). Mass spectrum: 457 [M+1]$^+$.

EXAMPLE 6

7-Methyl[1,4]benzodioxino[2,3-a]pyrrolo[3,4-c] carbazole-6,8-(7H,13H)-dione

Step A: 3-(1,4-Benzodioxin-2-yl)-4-(1H-indol-3-yl)-1-methyl-1H-pyrrole-2,5-dione 331.54 μmol of the compound of Step A of Example 5 are dissolved in 9 ml of formic acid. The reaction mixture is stirred under an inert atmosphere and at ambient temperature for 3 hours 30 minutes. The solvent is removed under reduced pressure; the residue is then washed, filtered and rinsed with methanol and is then dried in vacuo, allowing the expected product to be isolated.

Melting point: 219° C. IR (KBr): $v_{C=O}$=1697 cm$^{-1}$. Mass spectrum: 359.5 [M+1]$^+$.

Step B: 7-Methyl[1,4]benzodioxino[2,3-a]pyrrolo[3, 4-c]carbazole-6,8(7H,13H)-dione 418.5 μmol of the compound obtained in Step A above are dissolved in 50 ml of toluene in an irradiation reactor and then 5.91 mmol of double-sublimed iodine are introduced into the reaction mixture. Irradiation is carried out at 500 W for 1 hour 10 minutes. The reaction mixture is then diluted with ethyl acetate, after which it is washed with 80 ml of 20% aqueous sodium thiosulphate solution until the organic phase is decolourised. The aqueous phase is extracted three times with ethyl acetate; the organic phases are then combined and directly concentrated. The solid residue obtained is washed firstly with diethyl ether and then filtered. It is washed subsequently with ethyl acetate and then with tetrahydrofuran and filtered. Purification by flash chromatography over silica gel (petroleum ether/ethyl acetate: 6/4) allows the expected product to be obtained.

Melting point: >355° C. IR (KBr): $v_{C=O}$=1692, 1703 cm$^{-1}$; $v_{NH}$=3343 cm$^{-1}$. Mass spectrum: 357 [M+1]$^+$.

EXAMPLE 7

7-[2-(Dimethylamino)ethyl][1,4]benzodioxino[2,3-a] pyrrolo[3,4-c]-carbazole-6,8(7H,13H)-dione 238.5 μmol of the compound of Example 6 are dissolved in 4 ml of N,N-dimethylethylenediamine. The reaction mixture is heated at reflux for 16 hours and it is then cooled and concentrated. The residue obtained is washed, filtered and rinsed with methanol before being dried in vacuo, allowing the expected product to be isolated.

Melting point: 298° C. (decomposition). IR (KBr): $v_{C=O}$=1703, 1753 cm$^{-1}$; $v_{NH}$=3441 cm$^{-1}$. Mass spectrum: 414 [M+1]$^+$.

EXAMPLE 8

7,13-Dimethyl[1,4]benzodioxino[2,3-a]pyrrolo[3,4-c]carbazole-6,8-(7H,13H)-dione

Step A: 3-(1,4-Benzodioxin-2-yl)-1-methyl-4-(1-methyl-1H-indol-3-yl)-1H-pyrrole-2,5-dione 69.76 μmol of the compound obtained in Step A of Example 6, 111.62 μmol of sodium hydroxide, 7.46 μmol of benzyltriethylammonium chloride and 418.58 mmol of methyl iodide are dissolved in 0.5 ml of dichloromethane. The reaction mixture is stirred at ambient temperature for 1 hour 45 minutes, and then the solvent is removed in vacuo. Purification by flash chromatography over silica gel (from petroleum ether/ethyl acetate: 7/3 to ethyl acetate) allows the expected product to be obtained.

Melting point: 204° C. (decomposition). IR (KBr): $v_{C=O}$=1697 cm$^{-1}$. Mass spectrum: 373 [M+1]$^+$.

Step B: 7,13-Dimethyl[1,4]benzodioxino[2,3-a]pyrrolo[3,4-c]carbazole-6,8-(7H,13H)-dione The expected product is obtained according to the procedure described in Step B of Example 5, starting from the compound obtained in Step A above.

EXAMPLE 9

13-Ethyl-7-methyl[1,4]benzodioxino[2,3-a]pyrrolo [3,4-c]carbazole-6,8(7H,13H)-dione Step A: 3-(1,4-Benzodioxin-2-yl)-4-(1-ethyl-1H-indol-3-yl)-1-methyl-1H-pyrrole-2,5-dione The expected product is obtained according to the procedure described in Step A of Example 8, starting from the compound obtained in Step A of Example 6 and replacing the methyl iodide with ethyl iodide.

Step B: 13-Ethyl-7-methyl[1,4]benzodioxino[2,3-a] pyrrolo[3,4-c]carbazole-6,8(7H,13H)dione The expected product is obtained according to the procedure described in Step B of Example 6, starting from the compound obtained in Step A above.

EXAMPLE 10

Naphtho[2',3':5,6][1,4]dioxino[2,3-a]pyrrolo[3,4-c]carbazole-5,7-(6H,16H)-dione

Step A: 3-(1H-Indol-3-yl)-4-naphtho[2,3-b][1,4]dioxin-2-yl-1H-pyrrole-2,5-dione The expected product is obtained according to the procedure described in Step A of Example 5, starting from the compounds of Preparations B and F.

Melting point: 261° C. IR (KBr): $v_{C=O}$=1759 cm$^{-1}$; $v_{NH}$=3171, 3398 cm$^{-1}$. Mass spectrum: 395 [M+1]$^+$.

Step B: Naphtho[2',3':5,6][1,4]dioxino[2,3-a]pyrrolo[3,4-c]carbazole-5,7(6H,16H)-dione The expected product is obtained according to the procedure described in Step B of Example 6, starting from the compound obtained in the Step above.

EXAMPLE 11

10-Fluoro-7-methyl[1,4]benzodioxino[2,3-a]pyrrolo[3,4-c]carbazole-6,8(7H,13H)-dione

Step A: 3-(1,4-Benzodioxin-2-yl)-4-(5-fluoro-1H-indol-3-yl)-1-methyl-1H-pyrrole-2,5-dione The expected product is obtained according to the procedure described in Step A of Example 5, starting from the compound of Preparation G.

Melting point: 229° C. IR (KBr): $v_{C=O}$=1698 cm$^{-1}$; $v_{NH}$=3380 cm$^{-1}$. Mass spectrum: 377 [M+1]$^+$.

Step B: 10-Fluoro-7-methyl[1,4]benzodioxino[2,3-a]pyrrolo[3,4-c]carbazole-6,8(7H,13H)-dione The expected product is obtained according to the procedure described in Step B of Example 6, starting from the compound obtained in Step A above.

Melting point: >355° C. IR (KBr): $v_{C=O}$=1699, 1753 cm$^{-1}$; $v_{NH}$=3339 cm$^{-1}$. Mass spectrum: 375 [M+1]$^+$.

EXAMPLE 12

7-[2-(Dimethylamino)ethyl]-10-fluoro[1,4]benzodioxino[2,3-a]-pyrrolo[3,4-c]carbazole-6,8(7H,13H)-dione The expected product is obtained according to the procedure described in Example 7, starting from the compound of Example 11.

Melting point: 337° C. (decomposition). IR (KBr): $v_{C=O}$=1701, 1755 cm$^{-1}$; $v_{NH}$=3447 cm$^{-1}$. Mass spectrum: 432 [M+1]$^+$.

EXAMPLE 13

11-Fluoro-7-methyl[1,4]benzodioxino[2,3-a]pyrrolo[3,4-c]carbazole-6,8(7H,13H)-dione

Step A: 3-(1,4-Benzodioxin-2-yl)-4-(6-fluoro-1H-indol-3-yl)-1-methyl-1H-pyrrole-2,5-dione The expected product is obtained according to the procedure described in Step A of Example 5, starting from the compound of Preparation H.

Melting point: 214° C. IR (KBr): $v_{C=O}$=1693 cm$^{-1}$; $v_{NH}$=3322 cm$^{-1}$. Mass spectrum: 377 [M+1]$^+$.

Step B: 11-Fluoro-7-methyl[1,4]benzodioxino[2,3-a]pyrrolo[3,4-c]carbazole-6,8-(7H,13H)-dione The expected product is obtained according to the procedure described in Step B of Example 6, starting from the compound obtained in Step A above.

Melting point: >360° C. IR (KBr): $v_{C=O}$=1697, 1752 cm$^{-1}$; $v_{NH}$=3349 cm$^{-1}$. Mass spectrum: 375 [M+1]$^+$.

EXAMPLE 14

7-[2-(Dimethylamino)ethyl]-11-fluoro[1,4]benzodioxino[2,3-a]-pyrrolo[3,4-c]carbazole-6,8(7H,13H)-dione The expected product is obtained according to the procedure described in Example 7, starting from the compound of Example 13.

Melting point: 301° C. (decomposition). IR (KBr): $v_{C=O}$=1703, 1752 cm$^{-1}$; $v_{NH}$=3439 cm$^{-1}$. Mass spectrum: 432 [M+1]$^+$.

EXAMPLE 15

10-Fluoro[1,4]benzodioxino[2,3-a]pyrrolo[3,4-c]carbazole-6,8-(7H,13H)-dione

Step A: 3-(1,4-Benzodioxin-2-yl)-4-(5-fluoro-1H-indol-3-yl)-1H-pyrrole-2,5-dione The expected product is obtained according to the procedure described in Step A of Example 5, starting from the compound of Preparation I.

Melting point: 241° C. (decomposition). IR (KBr): $v_{C=O}$=1693 cm$^{-1}$; $v_{NH}$=3177, 3335 cm$^{-1}$. Mass spectrum: 363 [M+1]$^+$.

Step B: 10-Fluoro[1,4]benzodioxino[2,3-a]pyrrolo[3,4-c]carbazole-6,8(7H,13H)-dione The expected product is obtained according to the procedure described in Step B of Example 6, starting from the compound obtained in Step A above.

Melting point: >360° C. IR (KBr): $v_{C=O}$=1707 cm$^{-1}$; $v_{NH}$=3258, 3379 cm$^{-1}$. Mass spectrum: 361 [M+1]$^+$.

EXAMPLE 16

11-Fluoro[1,4]benzodioxino[2,3-a]pyrrolo[3,4-c]carbazole-6,8-(7H,13H)-dione

Step A: 3-(1,4-Benzodioxin-2-yl)-4-(6-fluoro-1H-indol-3-yl)-1H-pyrrole-2,5-dione The expected product is obtained according to the procedure described in Step A of Example 5, starting from the compound of Preparation J.

Melting point: 203° C. IR (KBr): $v_{C=O}$=1697, 1762 cm$^{-1}$; $v_{NH}$=3179, 3344 cm$^{-1}$. Mass spectrum: 363 [M+1]$^+$.

Step B: 11-Fluoro[1,4]benzodioxino[2,3-a]pyrrolo[3,4-c]carbazole-6,8-(7H,13H)-dione The expected product is obtained according to the procedure described in Step B of Example 6, starting from the compound obtained in Step A above.

EXAMPLE 17 tert-Butyl 10-(benzyloxy)-7-methyl-6,8-dioxo-7,8-dihydro[1,4]benzo-dioxino[2,3-a]pyrrolo[3,4-c]carbazole-13(6H)-carboxylate Step A: tert-Butyl 3-[4-(1,4-benzodioxin-2-yl)-1-methyl-2,5-dioxo-2,5-dihydro-1H-pyrrol-3-yl]-5-(benzyloxy)-1H-indole-1-carboxylate The expected product is obtained according to the procedure described in Step A of Example 5, starting from the compound of Preparation K.

Melting point: 93° C. IR (KBr): $v_{C=O}$=1703, 1706, 1737, 1741 cm$^{-1}$. Mass spectrum: 565.5 [M+1]$^+$.

Step B: tert-Butyl 10-(benzyloxy)-7-methyl-6,8-dioxo-7,8-dihydro[1,4]-benzodioxino[2,3-a]pyrrolo[3,4-c]carbazole-13(6H)-carboxylate 177.1 μmol of the compound obtained in Step A above and 5.91 mmol of double-sublimed iodine are dissolved in 500 ml of toluene inside the cell of an irradiation apparatus. After irradiating for 40 minutes at 500 W, with stirring, the reaction mixture is cooled and then diluted with ethyl acetate. Washing with 80 ml of 20% aqueous sodium thiosulphate solution is carried out until the organic phase is decolourised. The aqueous phase is extracted with ethyl acetate three times, and then the organic phases are combined and directly concentrated in vacuo. The procedure is repeated a further two times in the same manner, using the same amounts. The crude reaction products of the three procedures are combined and the brown solid obtained is washed, filtered and rinsed with methanol before being dried in vacuo, allowing the expected product to be isolated.

Melting point: 302° C. (decomposition). IR (KBr): $v_{C=O}$=1705, 1731, 1760 cm$^{-1}$. Mass spectrum: 463 [M-Boc+1]$^+$.

EXAMPLE 18

10-Hydroxy-7-methyl[1,4]benzodioxino[2,3-a]pyrrolo[3,4-c]-carbazole-6,8(7H,13H)-dione 44.4 μmol of the compound of Example 17 are dissolved, under an inert atmosphere, in 3.5 ml of anhydrous dichloromethane. A 1M solution of boron tribromide in dichloromethane (89 μmol) is then added dropwise and with vigorous stirring to the solution, which has been cooled to 0° C. The reaction mixture is stirred at 0° C. for 15 minutes and then for 1 hour 15 minutes whilst being allowed to return to ambient temperature. After hydrolysis with distilled water, the reaction mixture is diluted with ethyl acetate, and the aqueous phase is extracted three times with ethyl acetate. The organic phases are combined and evaporated to dryness. The residue obtained is washed, filtered and rinsed with methanol and is then dried in vacuo, allowing the expected product to be isolated.

Melting point: >350° C. IR (KBr): $v_{C=O}$=1691, 1749 cm$^{-1}$; $v_{OH,NH}$=3345 cm$^{-1}$. Mass spectrum: 373 [M+1]$^+$.

EXAMPLE 19

10-(Benzyloxy)-7-[2-(dimethylamino)ethyl][1,4]benzodioxino[2,3-a]-pyrrolo[3,4-c]carbazole-6,8(7H,13H)-dione The expected product is obtained according to the procedure described in Example 7, starting from the compound of Example 17.

Melting point: 254° C. (decomposition). IR (KBr): $v_{C=O}$=1701, 1751 cm$^{-1}$; $v_{NH}$=3433 cm$^{-1}$. Mass spectrum: 520.5 [M+1]$^+$.

EXAMPLE 20

7-[2-(Dimethylamino)ethyl]-10-hydroxy[1,4]benzodioxino[2,3-a]-pyrrolo[3,4-c]carbazole-6,8(7H,13H)-dione The expected product is obtained according to the procedure described in Example 18, starting from the compound of Example 19.

Melting point: >360° C. IR (KBr): $v_{C=O}$=1697 cm$^{-1}$; $v_{OH,NH}$=3447 cm$^{-1}$. Mass spectrum: 430 [M+1]$^+$.

EXAMPLE 21 tert-Butyl 11-(benzyloxy)-7-methyl-6,8-dioxo-7,8-dihydro[1,4]-benzodioxino[2,3-a]pyrrolo[3,4-c]carbazole-13(6H)-carboxylate Step A: tert-Butyl 3-[4-(1,4-benzodioxin-2-yl)-1-methyl-2,5-dioxo-2,5-dihydro-1H-pyrrol-3-yl]-6-(benzyloxy)-1H-indole-1-carboxylate The expected product is obtained according to the procedure described in Step A of Example 5, starting from the compound of Preparation L.

Melting point: 88° C. IR (KBr): $v_{C=O}$=1703, 1737 cm$^{-1}$. Mass spectrum: 565 [M+1]$^+$.

Step B: tert-Butyl 11-(benzyloxy)-7-methyl-6,8-dioxo-7,8-dihydro[1,4]benzo-dioxino[2,3-a]pyrrolo[3,4-c]carbazole-13(6H)-carboxylate The expected product is obtained according to the procedure described in Step B of Example 17, starting from the compound obtained in Step A above.

Melting point: 204° C. IR (KBr): $v_{C=O}$=1703, 1747 cm$^{-1}$. Mass spectrum: 463 [M-Boc+1]$^+$.

EXAMPLE 22

11-Hydroxy-7-methyl[1,4]benzodioxino[2,3-a]pyrrolo[3,4-c]-carbazole-6,8(7H,13H)-dione The expected product is obtained according to the procedure described in Step B of Example 18, starting from the compound of Example 21.

Melting point: 360° C. IR (KBr): $v_{C=O}$=1684, 1696, 1737 cm$^{-1}$; $v_{OH,NH}$=3317, 3442 cm$^{-1}$. Mass spectrum: 373 [M+1]$^+$.

EXAMPLE 23

11-(Benzyloxy)-7-[2-(dimethylamino)ethyl][1,4]
benzodioxino[2,3-a]-pyrrolo[3,4-c]carbazole-6,8(7H,
13H)-dione The expected product is obtained according to the procedure described in Example 7, starting from the compound of Example 21.

Melting point: 262° C. (decomposition). IR (KBr): $\nu_{C=O}$=1701, 1750 cm$^{-1}$; $\nu_{OH,NH}$=3432 cm$^{-1}$. Mass spectrum: 520.5 [M+1]$^+$.

EXAMPLE 24

7-[2-(Dimethylamino)ethyl]-11-hydroxy[1,4]benzo-
dioxino[2,3-a]-pyrrolo[3,4-c]carbazole-6,8(7H,13H)-
dione The expected product is obtained according to the procedure described in Example 18, starting from the compound of Example 23.

Melting point: >360° C. IR (KBr): $\nu_{C=O}$=1686 cm$^{-1}$; $\nu_{OH,NH}$=3405 cm$^{-1}$. Mass spectrum: 430 [M+1]$^+$.

EXAMPLE 25 tert-Butyl 10-(benzyloxy)-6,8-dioxo-7,8-dihydro[1,
4]benzo-dioxino[2,3-a]pyrrolo[3,4-c]carbazole-13
(6H)-carboxylate Step A: tert-Butyl 3-[4-(1,4-benzodioxin-2-yl)-1-
(tert-butoxycarbonyl)-2,5-dioxo-2,5-dihydro-1H-
pyrrol-3-yl]-5-(benzyloxy)-1H-indole-1-carboxylate The expected product is obtained according to the procedure described in Step A of Example 5, starting from the compound of Preparation M.

Melting point: 76° C. IR (KBr): $\nu_{C=O}$=1741, 1763, 1797 cm$^{-1}$. Mass spectrum: 551.5 [M-Boc+1]$^+$.

Step B: tert-Butyl 10-(benzyloxy)-6,8-dioxo-7,8-
dihydro[1,4]benzodioxino[2,3-a]-pyrrolo[3,4-c]car-
bazole-13(6H)-carboxylate The expected product is obtained according to the procedure described in Step B of Example 6, starting from the compound obtained in Step A above.

Melting point: >304° C. IR (KBr): $\nu_{C=O}$=1719, 1731 cm$^{-1}$; $\nu_{NH}$=3198 cm$^{-1}$. Mass spectrum: 549.5 [M+1]$^+$.

EXAMPLE 26

10-Hydroxy[1,4]benzodioxino[2,3-a]pyrrolo[3,4-c]
carbazole-6,8-(7H,13H)-dione

The expected product is obtained according to the procedure described in Example 8, starting from the compound of Example 25.

Melting point: >360° C. IR (KBr): $\nu_{C=O}$=1712, 1750 cm$^{-1}$; $\nu_{NH,OH}$=3061, 3218, 3442 cm$^{-1}$. Mass spectrum: 359 [M+1]$^+$.

EXAMPLE 27 tert-Butyl 11-(benzyloxy)-6,8-dioxo-7,8-dihydro[1,
4]benzo-dioxino[2,3-a]pyrrolo[3,4-c]carbazole-13
(6H)-carboxylate Step A: tert-Butyl 3-[4-(1,4-benzodioxin-2-yl)-1-
(tert-butoxycarbonyl)-2,5-dioxo-2,5-dihydro-1H-
pyrrol-3-yl]-6-(benzyloxy)-1H-indole-1-carboxylate The expected product is obtained according to the procedure described in Step A of Example 5, starting from the compound of Preparation N.

Melting point: 81° C. IR (KBr): $\nu_{C=O}$=1716, 1739, 1762 cm$^{-1}$. Mass spectrum: 551.5 [M-Boc+1]$^+$.

Step B: tert-Butyl 11-(benzyloxy)-6,8-dioxo-7,8-
dihydro[1,4]benzodioxino[2,3-a]-pyrrolo[3,4-c]car-
bazole-13(6H)-carboxylate The expected product is obtained according to the procedure described in Step B of Example 6, starting from the compound obtained in Step A above.

Melting point: 199° C. IR (KBr): $\nu_{C=O}$=1731, 1761 cm$^{-1}$; $\nu_{NH}$=3384 cm$^{-1}$. Mass spectrum: 549.5 [M+1]$^+$.

EXAMPLE 28

11-Hydroxy[1,4]benzodioxino[2,3-a]pyrrolo[3,4-c]
carbazole-6,8(7H,13H)-dione

The expected product is obtained according to the procedure described in Example 8, starting from the compound of Example 27.

Melting point: >340° C. IR (KBr): $\nu_{C=O}$=1711, 1745 cm$^{-1}$; $\nu_{OH,NH}$=3054, 3197, 3427 cm$^{-1}$. Mass spectrum: 359 [M+1]$^+$.

EXAMPLE 29 tert-Butyl 6-methyl-5,7-dioxo-6,7-dihydronaphtho
[2',3':5,6]-[1,4]dioxino[2,3-a]pyrrolo[3,4-c]carba-
zole-16(5H)-carboxylate Step A: tert-Butyl 3-(1-methyl-4-naphtho[2,3-b][1,
4]dioxin-2-yl-2,5-dioxo-2,5-dihydro-1H-pyrrol-3-
yl)-1H-indole-1-carboxylate The expected product is obtained according to the procedure described in Step A of Example 5, starting from the compound of Preparation B.

Melting point: 158° C. IR (KBr): $\nu_{C=O}$=1702, 1736 cm$^{-1}$. Mass spectrum: 409 [M-Boc+1]$^+$.

Step B: tert-Butyl 6-methyl-5,7-dioxo-6,7-dihy-
dronaphtho[2',3':5,6][1,4]dioxino-[2,3-a]pyrrolo[3,4-
c]carbazole-16(5H)-carboxylate The expected product is obtained according to the procedure described in Step B of Example 5, starting from the compound obtained in Step A above.

EXAMPLE 30 tert-Butyl 8-(benzyloxy)-4-(2-hydroxyphenoxy)-1,3-
dioxo-2,3-dihydropyrrolo[3,4-c]carbazole-6(1H)-
carboxylate The expected product is obtained in the course of purification of the compound of Step B of Example 27.

Melting point: 198° C. IR (KBr): $v_{C=O}$=1725, 1757 cm$^{-1}$; $v_{OH,NH}$=3277 cm$^{-1}$. Mass spectrum: 551.5 [M+1]$^+$.

EXAMPLE 31 tert-Butyl 9-(benzyloxy)-4-(2-hydroxyphenoxy)-2-methyl-1,3-dioxo-2,3-dihydropyrrolo[3,4-c]carbazole-6(1H)-carboxylate In an irradiation apparatus, 177.1 μmol of the compound obtained in Step A of Example 17 are dissolved in 500 ml of toluene and then 5.91 mmol of double-sublimed iodine are introduced into the reaction mixture. Irradiation is carried out at 500 W for 40 minutes. The reaction mixture is subsequently diluted with ethyl acetate and then washed with 80 ml of 20% aqueous sodium thiosulphate solution until the organic phase is decolourised. The aqueous phase is extracted with ethyl acetate three times, and then the organic phases are combined and directly concentrated to dryness in vacuo. The procedure is carried out a further three times in the same manner, using the same amounts. The crude reaction products of the four procedures are combined. The residue obtained is washed, filtered and rinsed with methanol and is then evaporated. Purification by flash chromatography over silica gel (petroleum ether/ethyl acetate: 4/6) allows the expected product to be isolated.

Melting point: 170° C. IR (KBr): $v_{C=O}$=1700, 1727, 1759 cm$^{-1}$; $v_{OH}$=3425 cm$^{-1}$. Mass spectrum: 565.0 [M+1]$^+$.

EXAMPLE 32

9-Hydroxy-4-(2-hydroxyphenoxy)-2-methylpyrrolo[3,4-c]-carbazole-1,3(2H,6H)-dione The expected product is obtained according to the procedure of Example 18, starting from the compound of Example 31.

Melting point: 277° C. (decomposition). IR (KBr): $v_{C=O}$=1698, 1757 cm$^{-1}$; $v_{OH,NH}$=3366 cm$^{-1}$. Mass spectrum: 375 [M+1]$^+$.

EXAMPLE 33 tert-Butyl 4-(2-hydroxyphenoxy)-2-methyl-1,3-dioxo-2,3-dihydropyrrolo[3,4-c]carbazole-6(1H)-carboxylate To a solution of 740.2 μmol of the compound of Preparation A in 12.5 ml of 1,4-dioxane there are added 616.9 μmol of the compound of Preparation E, 61.7 μmol of copper iodide and 61.7 μmol of tetrakis(triphenylphosphine)palladium. The reaction mixture is heated at 100° C., under an inert atmosphere, for 21 hours The solution is then filtered to remove the remnants of palladium and the filtrate is evaporated to dryness. Purification by flash chromatography over silica gel (petroleum ether/ethyl acetate: 7/3) allows the expected product to be obtained.

Melting point: 182° C. (decomposition). IR (KBr): $v_{C=O}$=1697, 1730, 1757 cm$^{-1}$; $v_{OH}$=3432 cm$^{-1}$. Mass spectrum: 459 [M+1]$^+$.

EXAMPLE 34 tert-Butyl 4-(2-methoxyphenoxy)-2-methyl-1,3-dioxo-2,3-dihydropyrrolo[3,4-c]carbazole-6(1H)-carboxylate To a solution of 152.68 μmol of the compound of Example 33 in 5 ml of acetone there are added 458.05 μmol of dry potassium carbonate and 763.41 μmol of methyl iodide. The reaction mixture is heated at reflux and stirred for 2 hours 25 minutes. The solvent is then removed in vacuo, and the collected residue is washed, filtered and rinsed with methanol before being dried in vacuo, allowing the expected product to be isolated.

Melting point: >333° C. IR (KBr): $v_{C=O}$=1705, 1724 cm$^{-1}$. Mass spectrum: 473.5 [M+1]$^+$.

EXAMPLE 35

4-(2-Methoxyphenoxy)-2-methylpyrrolo[3,4-c]carbazole-1,3(2H,6H)-dione 84.6 μmol of the compound of Example 34 are dissolved in 2 ml of trifluoroacetic acid and then the reaction mixture is stirred at ambient temperature for 3 hours. The acid is removed in vacuo, and the residue is then washed, filtered and rinsed with methanol before being dried in vacuo, allowing the expected product to be isolated.

Melting point: 228° C. IR (KBr): $v_{C=O}$=1698, 1753 cm$^{-1}$; $v_{NH}$=3341, 3643 cm$^{-1}$. Mass spectrum: 373 [M+1]$^+$.

EXAMPLE 36

4-(2-Hydroxyphenoxy)-2-methylpyrrolo[3,4-c]carbazole-1,3-(2H,6H)-dione 261.7 μmol of the compound of Example 33 are dissolved in 7 ml of formic acid; the reaction mixture is then stirred at ambient temperature for 18 hours. The acid is removed in vacuo and the residue is then washed, filtered and rinsed with methanol before being dried in vacuo, allowing the expected product to be isolated.

Melting point: 258° C. IR (KBr): $v_{C=O}$=1695, 1757 cm$^-$; $v_{OH,NH}$=3243, 3525 cm$^{-1}$. Mass spectrum: 359 [M+1]$^+$.

EXAMPLE 37 tert-Butyl 2-methyl-1,3-dioxo-4-(2-{[(trifluoromethyl)sulphonyl]-oxy}phenoxy)-2,3-dihydropyrrolo[3,4-c]carbazole-6(1H)-carboxylate 124.3 μmol of the compound of Example 33 are dissolved, under an anhydrous atmosphere, in 1 ml of dry dichloromethane. The temperature of the solution is lowered to 0° C. and then 161.5 μmol of triethylamine and 161.5 μmol of triflic anhydride are successively added dropwise to the reaction mixture, which is stirred for 1 hour 20 minutes from 0° C. to ambient temperature. After hydrolysis with distilled water, the reaction mixture is diluted with dichloromethane and then the aqueous phase is extracted three times with the same solvent. The organic phases are combined, dried over magnesium sulphate, filtered and concentrated. Purification by chromatography over silica gel (petroleum ether/ethyl acetate: 7/3) allows the expected product to be isolated.

Melting point: 182° C. IR (KBr): $v_{C=O}$=1710, 1737, 1766 cm$^{-1}$. Mass spectrum: 591 [M+1]$^+$.

EXAMPLE 38

2-[(2-Methyl-1,3-dioxo-1,2,3,6-tetrahydropyrrolo[3,4-c]carbazol-4-yl)oxy]phenyl trifluoromethanesulphonate Under an inert atmosphere, 67.7 μmol of the compound of Example 37 are dissolved in 1 ml of distilled dimethylformamide in the presence of 6.8 μmol of bis(triphenylphosphine)palladium chloride, 203.1 μmol of dry lithium chloride and 81.2 μmol of 1,8-diazabicyclo[5.4.0]undec-7-ene. After stirring at 140° C. for 4 hours 20 minutes, the reaction mixture is cooled and the dimethylformamide is then removed. Purification by chromatography over silica gel (petroleum ether/ethyl acetate: 6/4) allows the expected product to be isolated.

Melting point: 214° C. IR (KBr): $v_{C=O}$=1700–1708, 1757 cm$^{-1}$; $v_{NH}$=3430 cm$^{-1}$. Mass spectrum: 491 [M+1]$^+$.

EXAMPLE 39 tert-Butyl 8-(benzyloxy)-4-(2-hydroxyphenoxy)-2-methyl-1,3-dioxo-2,3-dihydropyrrolo[3,4-c]carbazole-6(1H)-carboxylate The expected product is obtained in the course of purification of the compound of Step B of Example 21.

Melting point: 191° C. IR (KBr): $v_{C=O}$=1701, 1734 cm$^{-1}$; $v_{OH}$=3425 cm$^{-1}$. Mass spectrum: 565 [M+1]$^+$.

EXAMPLE 40 tert-Butyl 8-(benzyloxy)-2-methyl-1,3-dioxo-4-(2-{[(trifluoro-methyl)sulphonyl]oxy}phenoxy)-2,3-dihydropyrrolo[3,4-c]-carbazole-6(1H)-carboxylate The expected product is obtained according to the procedure of Example 37, starting from the compound of Example 39.

Melting point: 186° C. IR (KBr): $v_{C=O}$=1703, 1714, 1724 cm$^{-1}$. Mass spectrum: 697 [M+1]$^+$.

EXAMPLE 41

8-Hydroxy-4-(2-hydroxyphenoxy)-2-methylpyrrolo[3,4-c]-carbazole-1,3(2H,6H)-dione The expected product is obtained according to the procedure of Example 18, starting from the compound of Example 39.

Melting point: 200° C. IR (KBr): $v_{C=O}$=1691 cm$^{-1}$; $v_{OH,NH}$=3399 cm$^{-1}$. Mass spectrum: 375 [M+1]$^+$.

EXAMPLE 42 tert-Butyl 12-(benzhydryloxy)-7-methyl-6,8-dioxo-7,8-dihydro[1,4]-benzodioxino[2,3-a]pyrrolo[3,4-c]carbazole-13(6H)-carboxylate Step A: tert-Butyl 7-(benzhydryloxy)-3-[4-(1,4-benzodioxin-2-yl)-1-methyl-2,5-dioxo-2,5-dihydro-1H-pyrrol-3-yl]-1H-indole-1-carboxylate The expected product is obtained according to the procedure described in Step A of Example 5, starting from the compound of Preparation O.

Melting point: 138° C. (decomposition). IR (KBr): $v_{C=O}$=1707, 1753 cm$^{-1}$. Mass spectrum: 641.5 [M+1]$^+$.

Step B: tert-Butyl 12-(benzhydryloxy)-7-methyl-6,8-dioxo-7,8-dihydro[1,4]benzo-dioxino[2,3-a]pyrrolo[3,4-c]carbazole-13(6H)-carboxylate The expected product is obtained according to the procedure described in Step B of Example 17, starting from the compound of Step A above.

Pharmacological Study of Compounds of the Invention

EXAMPLE 43

In vitro Activity

L1210 Murine Leukaemia

L1210 murine leukaemia was used in vitro. The cells are cultured in RPMI 1640 complete culture medium containing 10% foetal calf serum, 2 mM glutamine, 50 units/ml of penicillin, 50 μg/ml of streptomycin and 10 mM Hepes, pH=7.4. The cells are distributed on microplates and are exposed to the cytotoxic compounds for 4 doubling periods, or 48 hours. The number of viable cells is then quantified by a colorimetric assay, the Microculture Tetrazolium Assay (J. Carmichael et al., *Cancer Res.*; 47, 939–942 (1987)). The results are expressed as the IC$_{50}$, the concentration of cytotoxic agent which inhibits the treated cells by 50%. All the compounds of the invention exhibit good cytotoxicity with respect to this cell line. By way of example, the compound of Example 20 has an IC$_{50}$ of 0.074 μM with respect to L1210.

Human Cell Lines

The compounds of the invention were also tested on human cell lines originating from solid tumours, in accordance with the same test protocol as that described for L1210 murine leukaemia but with incubation periods of 4 days instead of 2 days. By way of illustration, the compound of Example 20 has an IC$_{50}$ of 190 nM with respect to DU145 prostate carcinoma and of the order of from 10 to 200 nM with respect to human lines originating from A549 non-small-cell lung carcinoma, HT-29 colon carcinoma and KB-3-1 epidermoid carcinoma.

EXAMPLE 44

Action on the Cell Cycle

L1210 cells are incubated for 21 hours at 37° C. in the presence of various concentrations of test compounds. The cells are then fixed by 70% (v/v) ethanol, washed twice in PBS and incubated for 30 minutes at 20° C. in PBS that contains 100 μg/ml of RNAse and 50 μg/ml of propidium iodide. The results are expressed in terms of the percentage of the cells that accumulate in the G2+M phase after 21 hours, compared with the control (control: 20%). The compounds of the invention are especially interesting, at a concentration of less than 2.5 μM causing accumulation of at least 70% of cells in the G2+M phase after 21 hours.

EXAMPLE 45

In vivo Activity

Anti-Tumour Activity on P 388 Leukaemia

Line P388 (murine leukaemia) was supplied by the National Cancer Institute (Frederick, USA). The tumour cells (10$^6$ cells) were inoculated on day 0 into the peritoneal cavity of female B6D2F1 mice (Iffa Credo, France). Six mice weighing from 18 to 20 g were used in each test group. The products were administered by the intraperitoneal route on day 1.

The anti-tumour activity is expressed as % T/C:

$$\% \ T/C \ (\text{mouse}) = \frac{\text{Median survival time of the treated animals}}{\text{Median survival time of the control animals}} \times 100$$

The results obtained show excellent in vivo activity in the P 388 leukaemia model, with a T/C of 210% for a dose of 50 mg/kg, along with low toxicity of the compounds, indicating an excellent therapeutic index.

EXAMPLE 46

Pharmaceutical Composition: Injectable Solution

Compound of Example 20 . . . 10 mg
Distilled water for injectable preparations . . . 0.25 ml

What is claimed is:
1. A compound selected from those of formula (I):

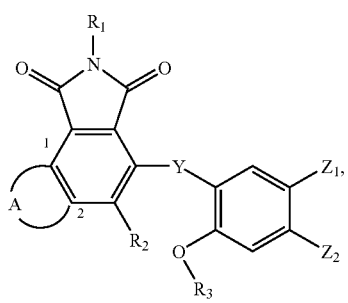

wherein
A, together with the carbon atoms to which it is bonded, represents a group of formula (a):

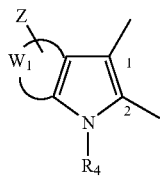

wherein:
$W_1$, together with the carbon atoms to which it is bonded, represents phenyl or pyridyl,
Z represents a group selected from hydrogen, halogen, linear or branched ($C_1$–$C_6$)alkyl, nitro, cyano, hydroxy, linear or branched ($C_1$–$C_6$)alkoxy, aryl, aryl-($C_1$–$C_6$)alkyl in which the alkyl moiety is linear or branched, aryloxy, aryl-($C_1$–$C_6$)alkoxy in which the alkoxy moiety is linear or branched and $NR_5R_6$ wherein $R_5$ and $R_6$, which may be identical or different, each represents a group selected from hydrogen and linear or branched ($C_1$–$C_6$)alkyl,
R4 represents a group selected from hydrogen, linear or branched ($C_1$–$C_6$)alkyl, aryl and aryl-($C_1$–$C_6$)alkyl in which the alkyl moiety is linear or branched or —C(O)—OR'$_5$ wherein R'$_5$ represents a group selected from linear or branched ($C_1$–$C_6$)alkyl, aryl and aryl-($C_1$–$C_6$)alkyl in which the alkyl moiety is linear or branched,
Y represents a group selected from oxygen or methylene,
$R_2$ and $R_3$ form a bond,
$R_1$ represents a group selected from hydrogen, linear or branched ($C_1$–$C_6$)alkyl, aryl, aryl-($C_1$–$C_6$)alkyl in which the alkyl moiety is linear or branched or linear or branched ($C_1$–$C_6$)alkylene substituted by one or more identical or different groups selected from —OR"$_5$ and —NR"$_5$R"$_6$ wherein R"$_5$ and R"$_6$ have the same meaning as $R_5$ and $R_6$ defined hereinbefore,
$Z_1$ and $Z_2$, each represent hydrogen or,
$Z_1$ and $Z_2$, together with the carbon atoms to which they are bonded, form phenyl,
it being understood that:
when Z represents hydrogen, $R_1$ is other than hydrogen,
and aryl may be a phenyl, naphthyl, dihydronaphthyl, tetrahydronaphthyl, indenyl or indanyl group, each of those groups being optionally substituted by one or more identical or different groups selected from halogen, linear or branched ($C_1$–$C_6$)alkyl, linear or branched ($C_1$–$C_6$)trihaloalkyl, hydroxy, linear or branched ($C_1$–$C_6$)alkoxy, and amino optionally substituted by one or two linear or branched ($C_1$–$C_6$)alkyl groups.

2. A compound of claim 1, which is a compound of formula (IA)

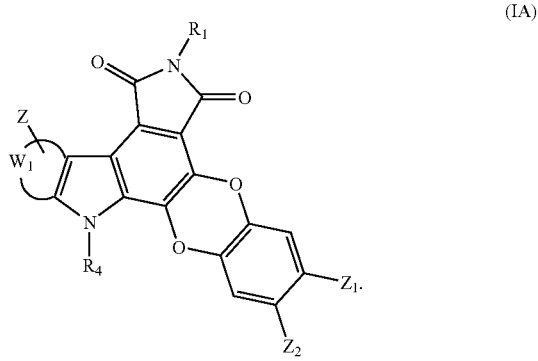

3. A compound of claim 1, which is a compound of formula (IB)

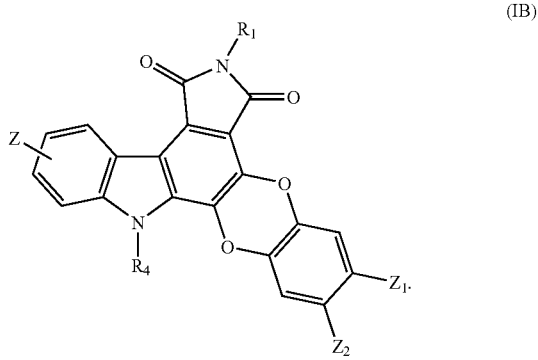

4. A compound of claim 1, which is a compound of formula (IC)

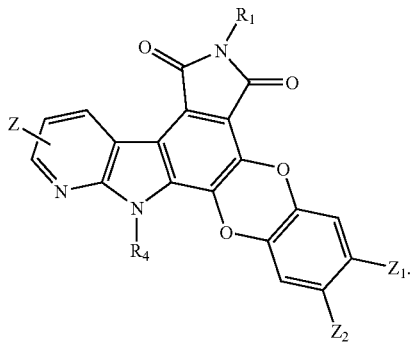

(IC)

5. A compound of claim 1, wherein Z represents hydrogen, halogen or hydroxy.

6. A compound of claim 1, wherein A, together with the carbon atoms to which it is bonded, represents a group of formula:

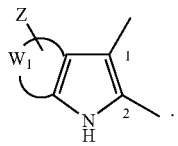

7. A compound of claim 1, wherein $R_1$ represents hydrogen or linear or branched $(C_1–C_6)$alkyl or linear or branched $(C_1–C_6)$alkylene substituted by one or more identical or different groups selected from $—NR_5R_6$ wherein $R_5$ and $R_6$ are as defined for formula (I).

8. A compound of claim 1, wherein $Z_1$ and $Z_2$ represent hydrogen.

9. A compound of claim 1, which is selected from:
  7-methyl[1,4]benzodioxino[2,3-a]pyrrolo[3,4-c]carbazole-6,8-dione,
  10-fluoro-7-methyl[1,4]benzodioxino[2,3-a]pyrrolo[3,4-c]carbazole-6,8-dione,
  11-fluoro-7-methyl[1,4]benzodioxino[2,3-a]pyrrolo[3,4-c]carbazole-6,8-dione,
  7-[2-(dimethylamino)ethyl]-10-fluoro[1,4]benzodioxino[2,3-a]pyrrolo[3,4-c]-carbazole-6,8-dione,
  10-hydroxy[1,4]benzodioxino[2,3-a]pyrrolo[3,4-c]carbazole-6,8-dione,
  11-hydroxy[1,4]benzodioxino[2,3-a]pyrrolo[3,4-c]carbazole-6,8-dione,
  7-[2-(dimethylamino)ethyl][1,4]benzodioxino[2,3-a]pyrrolo[3,4-c]carbazole-6,8-dione,
  7-[2-(dimethylamino)ethyl]-10-hydroxy[1,4]benzodioxino[2,3-c]-pyrrolo[3,4-c]-carbazole-6,8-dione, and
  7-[2-(dimethylamino)ethyl]-11-hydroxy[1,4]benzodioxino[2,3-a]pyrrolo[3,4-c]-carbazole-6,8-dione.

10. A method for treating a living animal body afflicted with a condition selected from leukemia, prostate carcinoma, non small-lung cell carcinoma, colon carcinoma, and epidermoid carcinoma, comprising the step of administering to the living animal body an amount of a compound of claim 1, which is effective for treatment of the condition.

11. A pharmaceutical composition comprising as active principle an effective amount of a compound of claim 1, together with one or more pharmaceutically acceptable excipients or vehicles.

12. The method of claim 10, wherein the living animal body is a human.

* * * * *